United States Patent [19]
Hermelin

[11] Patent Number: 5,945,123
[45] Date of Patent: Aug. 31, 1999

[54] MAXIMIZING EFFECTIVENESS OF SUBSTANCES USED TO IMPROVE HEALTH AND WELL BEING

[75] Inventor: Victor M. Hermelin, St. Louis, Mo.

[73] Assignee: K-V Pharmaceutical Company, St. Louis, Mo.

[21] Appl. No.: 09/053,487

[22] Filed: Apr. 2, 1998

[51] Int. Cl.⁶ .............................. A61K 9/14; A61K 9/28; A61K 9/48; A61K 9/52; A61K 9/02; A61K 9/06; A61K 9/08; A61K 9/10
[52] U.S. Cl. ...................... 424/464; 424/422; 424/423; 424/430; 424/433; 424/434; 424/436; 424/441; 424/443; 424/451; 424/455; 424/456; 424/458; 424/463; 424/464; 424/468; 424/472; 424/474; 424/489; 424/490; 514/937
[58] Field of Search ................................. 424/422, 433, 424/436, 441, 443, 451, 455, 456, 457, 464, 468, 472, 489, 423, 430, 434, 458, 463, 474, 490; 514/937

[56] References Cited

U.S. PATENT DOCUMENTS

| | | | |
|---|---|---|---|
| 4,182,756 | 1/1980 | Ramsay et al. | 424/180 |
| 4,464,170 | 8/1984 | Clemens et al. | 604/50 |
| 4,811,845 | 3/1989 | Baggett | 206/534 |
| 4,889,238 | 12/1989 | Batchelor | 206/535 |
| 4,981,468 | 1/1991 | Benefiel et al. | 604/83 |
| 5,047,007 | 9/1991 | McNichols et al. | 604/20 |
| 5,233,987 | 8/1993 | Fabian et al. | 607/41 |
| 5,494,678 | 2/1996 | Paradissis et al. | 424/439 |
| 5,521,208 | 5/1996 | York | 514/409 |
| 5,547,878 | 8/1996 | Kell | 436/111 |
| 5,597,072 | 1/1997 | Lieberman et al. | 206/534 |
| 5,652,146 | 7/1997 | Kell | 436/111 |
| 5,661,123 | 8/1997 | Stalker et al. | 514/2 |
| 5,763,396 | 6/1998 | Weiner et al. | 514/3 |
| 5,837,284 | 11/1998 | Mehta et al. | 424/459 |

OTHER PUBLICATIONS

*Physicians' Desk Reference (PDR)*, Fifty First Edition, 2573–2576 959–963, 1965–1970 418–422, 2844–2845 (1997).

Primary Examiner—Thurman K. Page
Assistant Examiner—James M. Spear
Attorney, Agent, or Firm—Gary M. Nath; Nath & Associates

[57] ABSTRACT

The present disclosure relates to novel dosage forms, drug delivery regimens, methods and pharmaceutical compositions which optimize the therapeutic effects of active therapeutic substances through the application of the concept of uneven dosing.

65 Claims, 10 Drawing Sheets

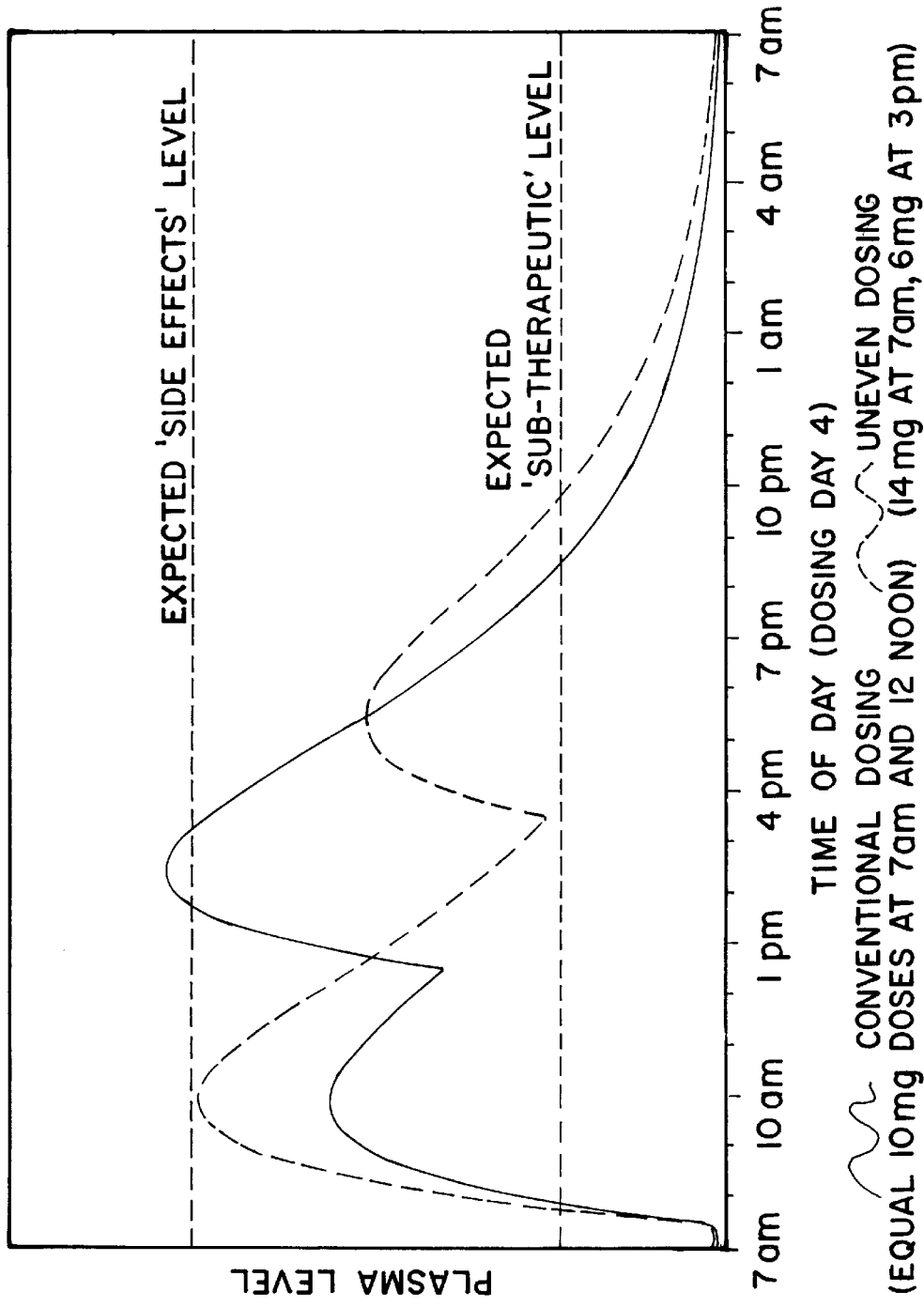

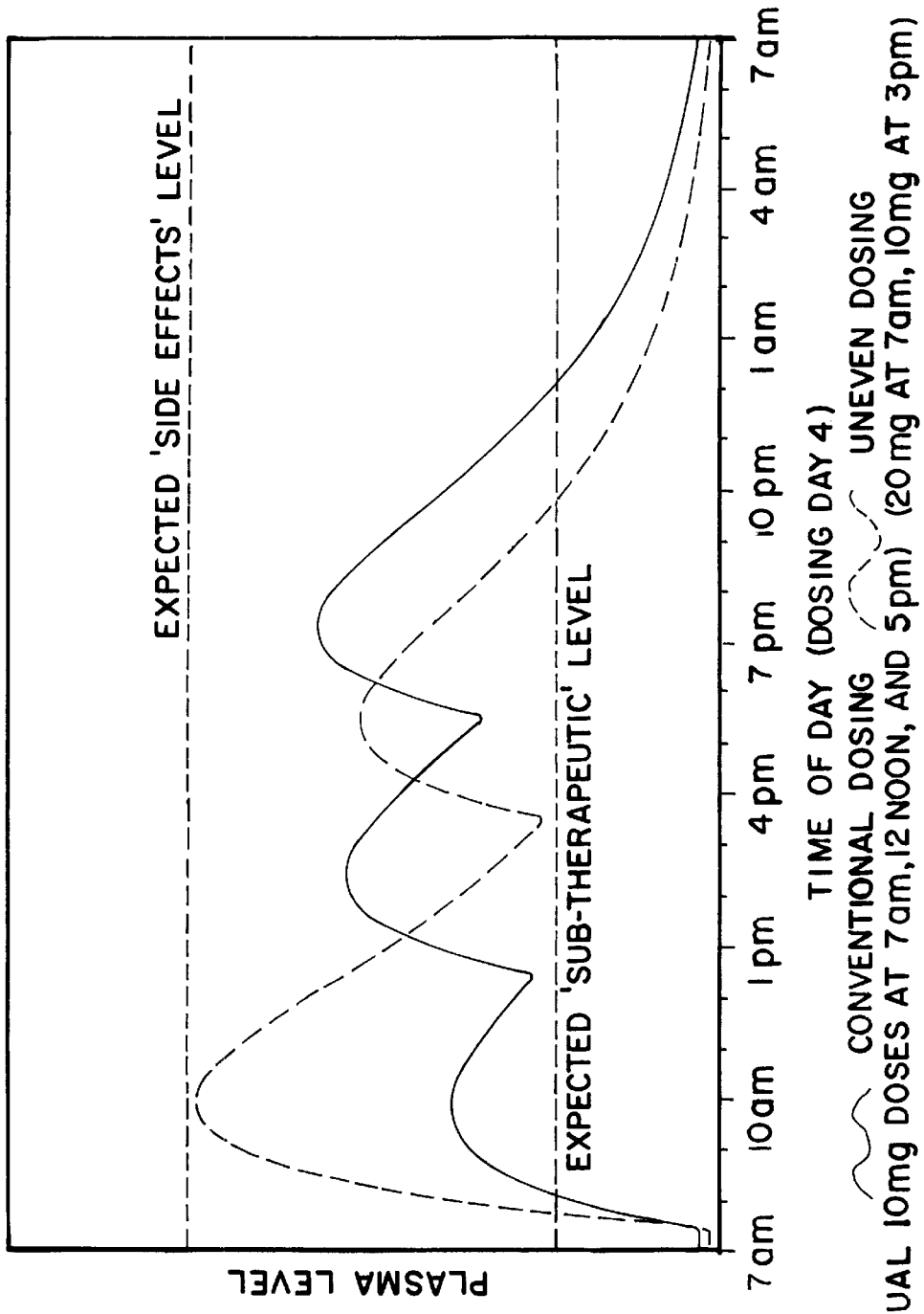

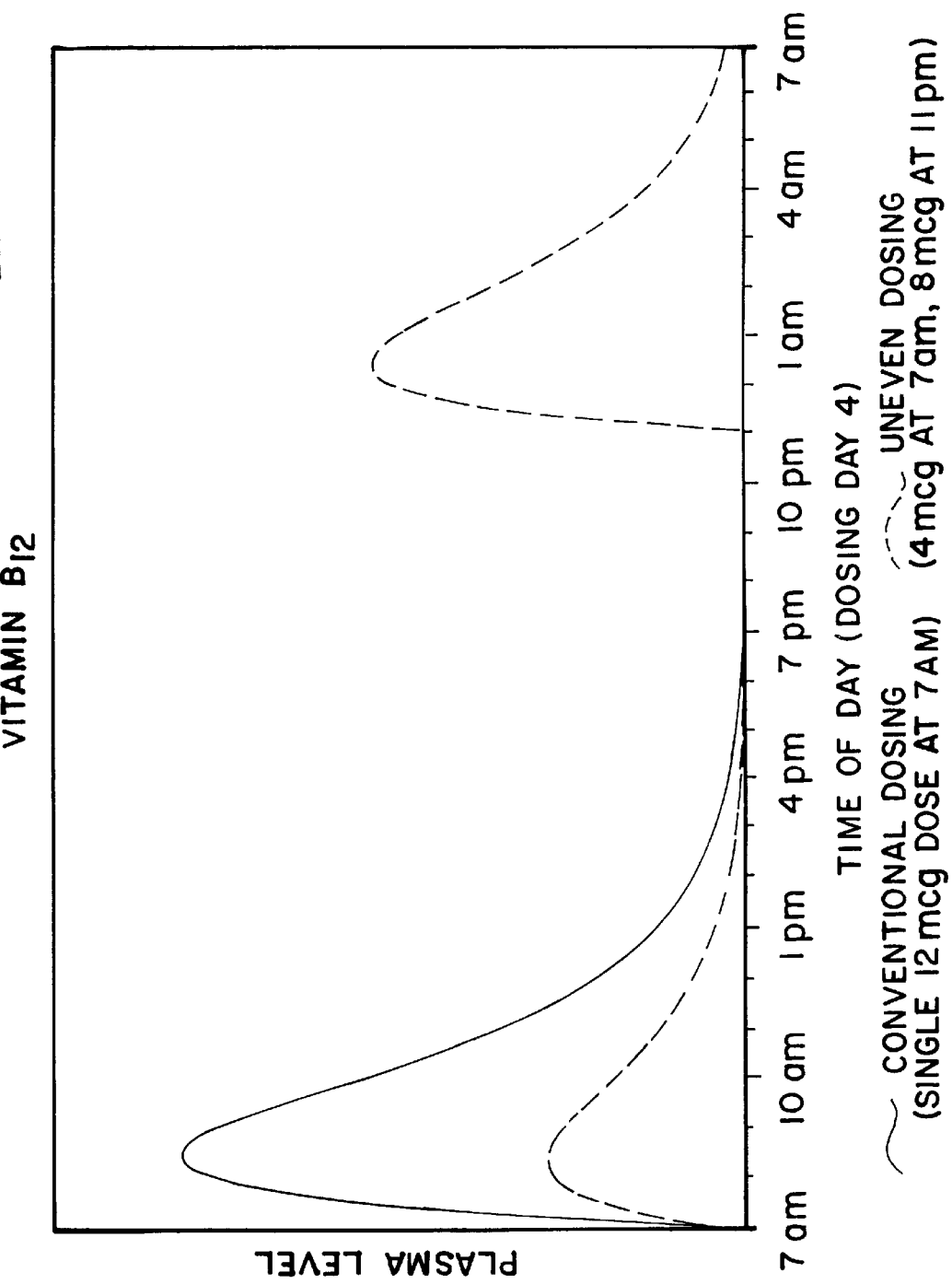

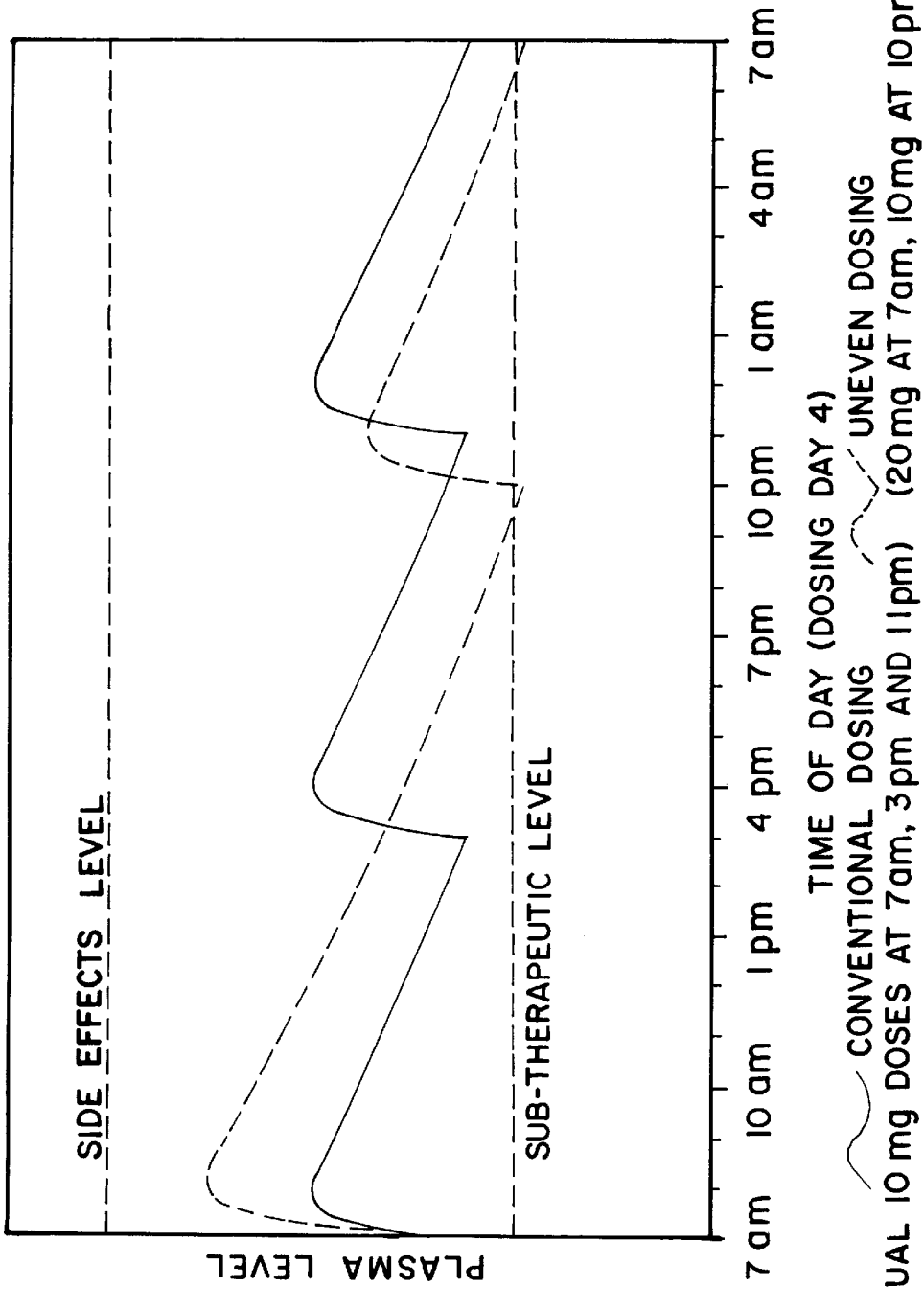

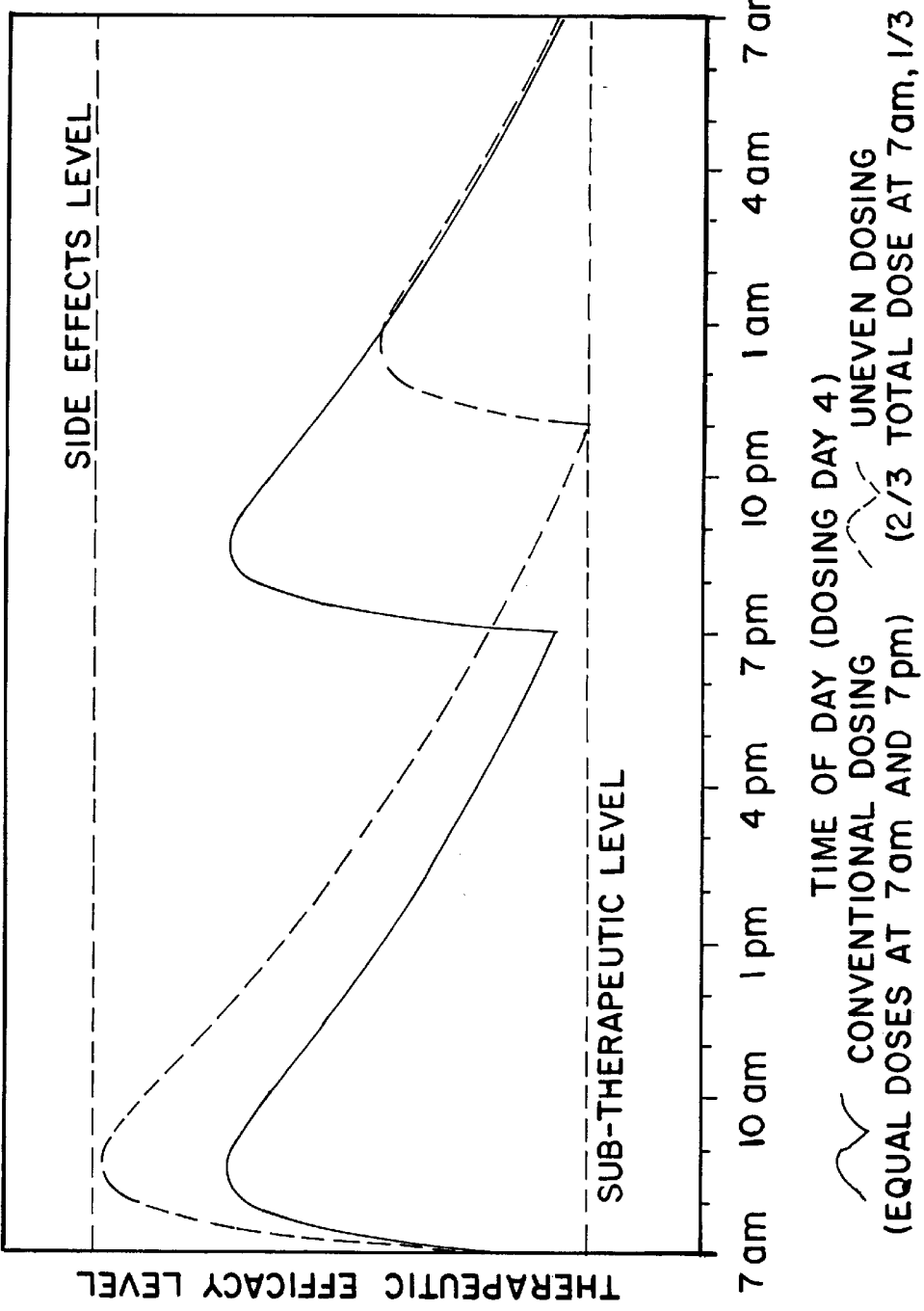

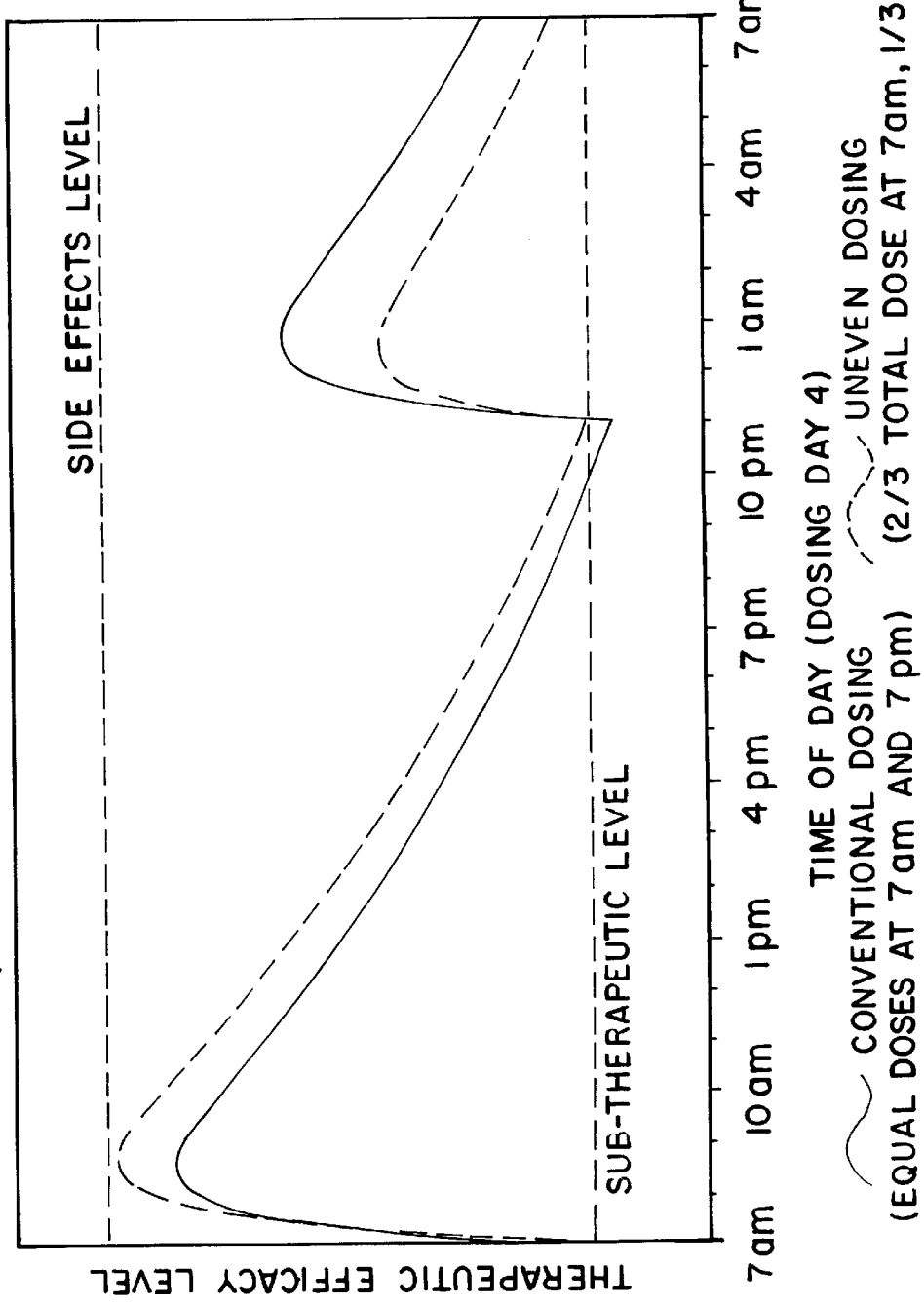

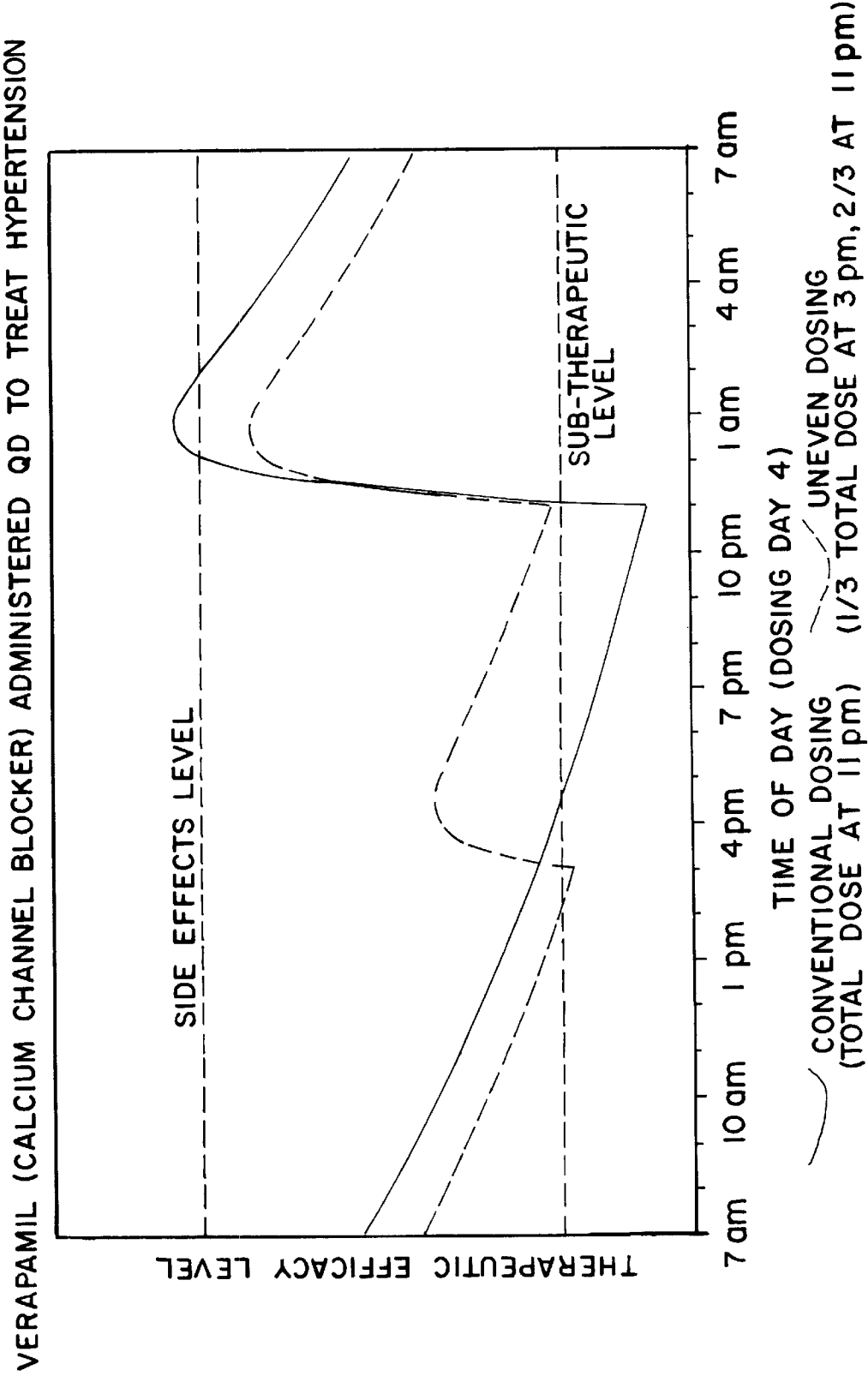

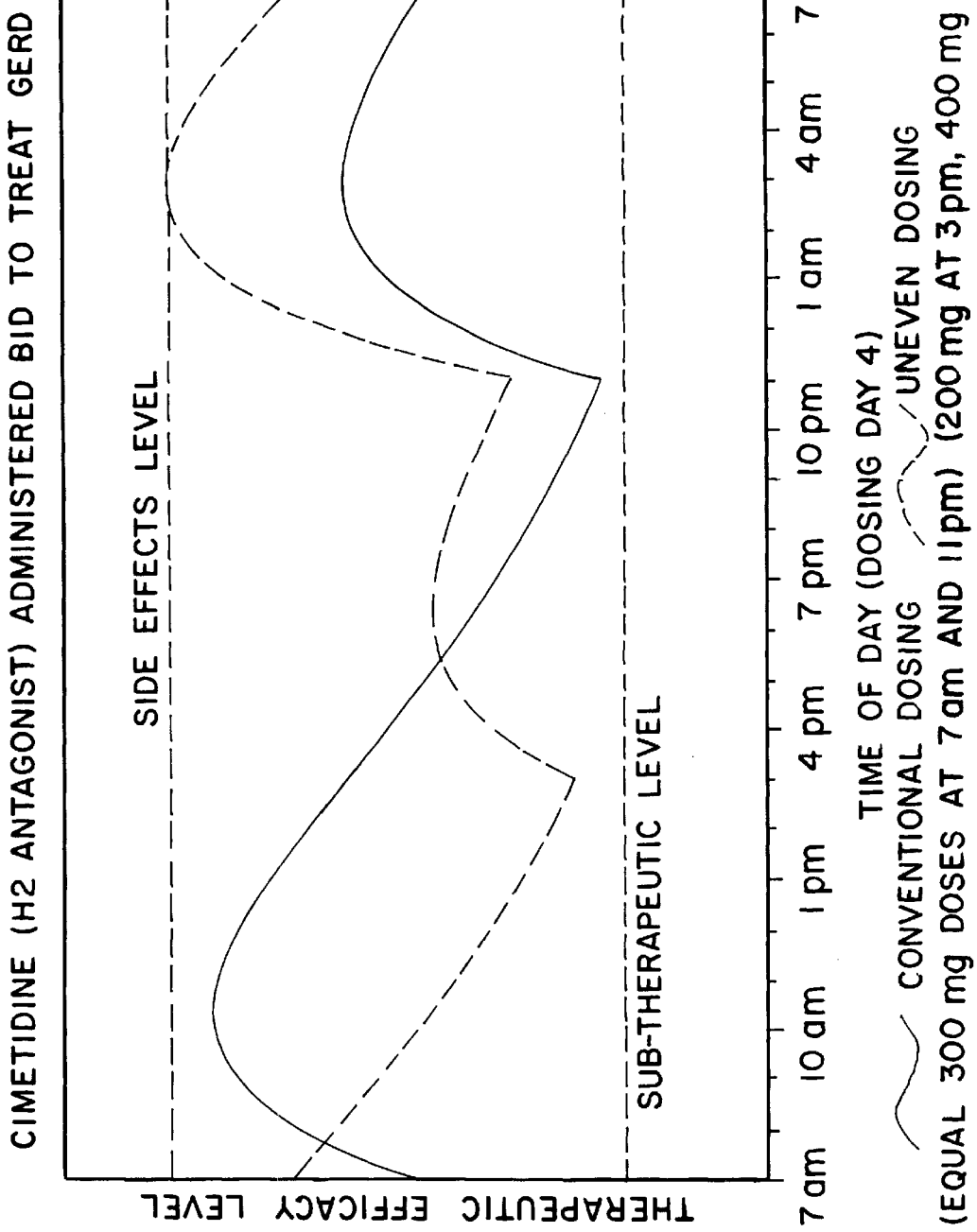

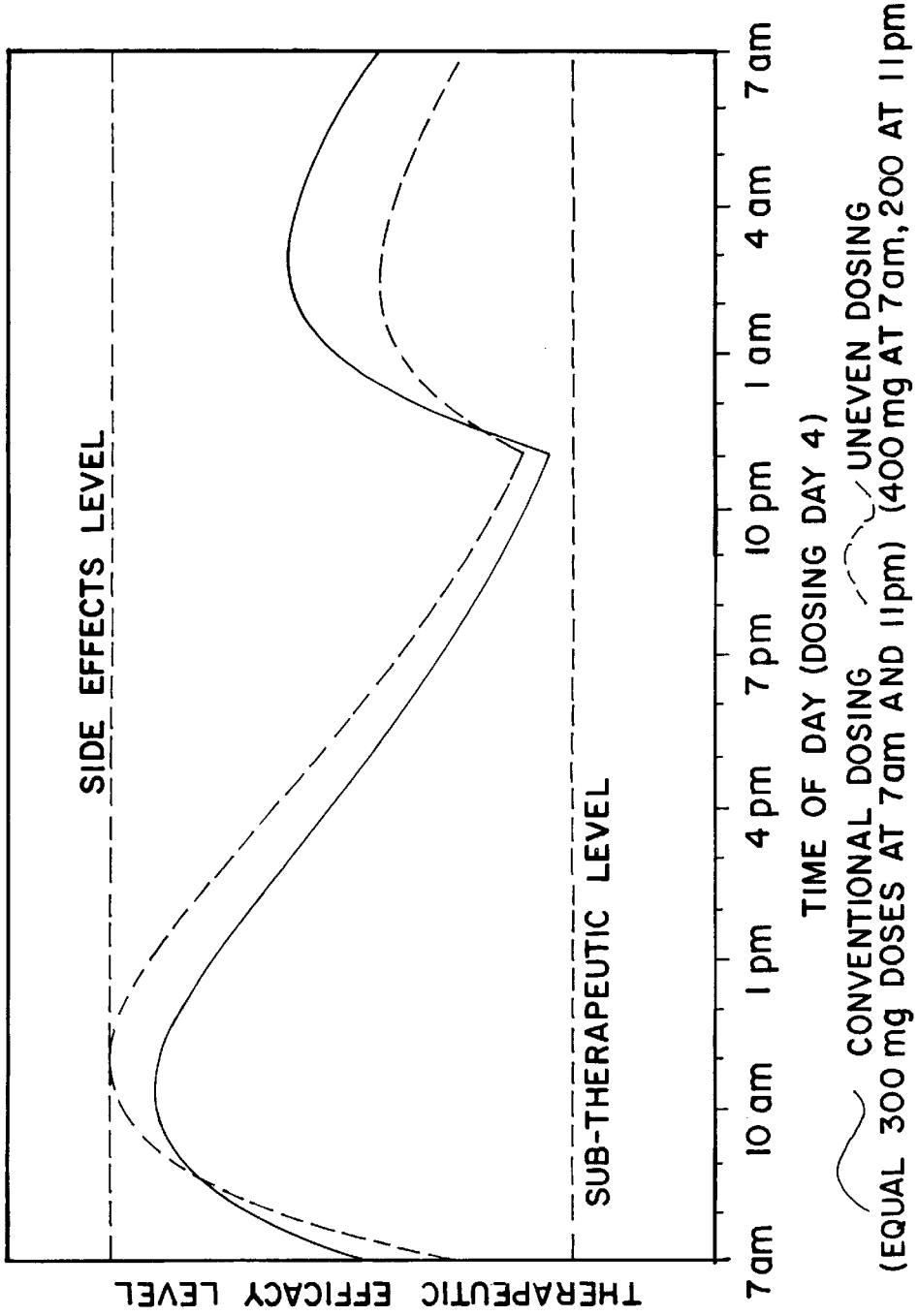

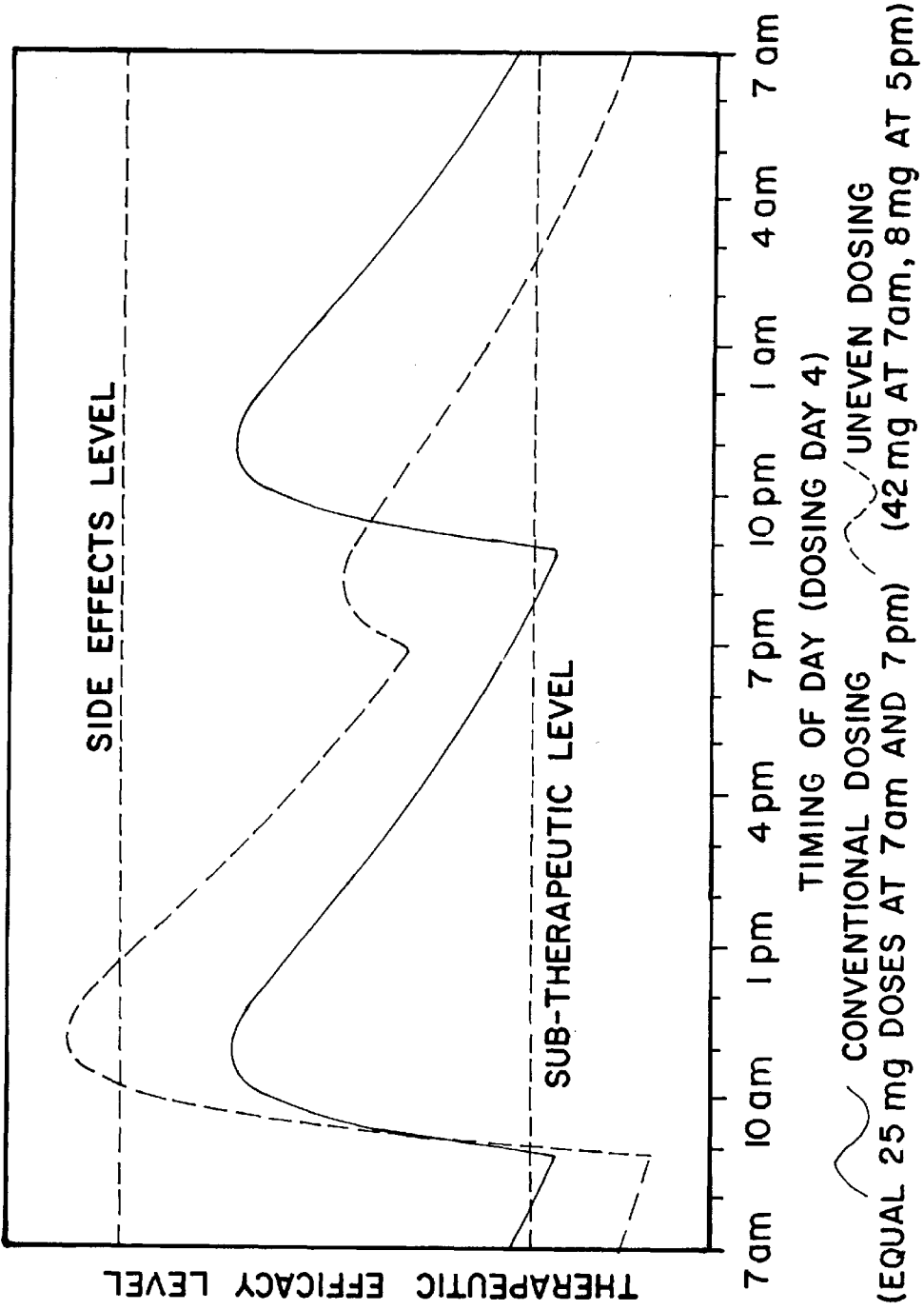

MAXIMIZING EFFECTIVENESS OF SUBSTANCES USED TO IMPROVE HEALTH AND WELL BEING

FIELD OF THE INVENTION

This invention relates to novel dosage forms, drug delivery regimens, methods and compositions which optimize therapeutic effects of biologically useful substances. The dosage forms, regimens, methods and pharmaceutical compositions of the present invention are adaptable to most biologically useful substances and will improve the effectiveness of said substances. The present invention is particularly useful for adaptation to the schedules, cycles and needs of individuals, thereby frequently improving compliance with their therapy, reducing amounts required daily to less than conventionally utilized, and minimizing undesired effects commonly experienced.

DESCRIPTION OF THE PRIOR ART

The administration of a substance to achieve a therapeutic objective generally requires the attainment and maintenance of a biologic response, which in turn requires an appropriate concentration of the active substance at a site of action. The appropriate dosage needed to achieve a therapeutic objective largely depends upon factors specific to the individual being treated, such as the individual's clinical state, the severity of the condition being treated, and the presence of other drugs and concurrent disease. Further, a proper dosage also depends upon factors specific to the individual substance being administered. These drug specific factors are characterized through two concepts: pharmacodynamics and pharmacokinetics.

Pharmacodynamics refers to the biologic response observed relative to the concentration at the active site. Pharmacokinetics refers to the attainment and maintenance of the appropriate concentration. Generally, once an individual's condition has been assessed and a substance is chosen for administration, a dosage amount will be selected by taking into consideration the known pharmacokinetic parameters of the substance in view of the individual's specific needs.

A substance may be administered to the individual in a number of dosage forms. For example, the dosage may be administered as a single dose in a given 24 hour period, in multiple doses throughout a 24 hour period, e.g., once a day, twice a day, or three times a day. Further, the dosage may be administered in immediate release, controlled release, sustained release, timed release, delayed release, extended release, long acting and other such forms. Regardless of which of the above forms is employed, presently used dosage forms generally fail to account for the effects of administration between time intervals of differing lengths, the time at which doses are administered, and the varying physiological needs of individuals throughout the course of a day.

For example, a common dosing regimen described in the medical literature is the 9-1-5-9 regimen in which equal doses of a drug are administered once every four hours during the 12 daylight hours of a 24 hour period (e.g., at 9:00 am, 1:00 pm, 5:00 pm and 9:00 pm), and no doses are administered during the following 12 nighttime hours. See *The Merck Manual*, Sixteenth Edition, 277:2623 (1992). Therefore, in the 9-1-5-9 regimen, an individual will receive the same amount of active therapeutic substance at 9:00 pm as at each of the other administrations, despite the substantially longer time interval of 8 hours following the 9:00 pm administration relative to the 4 hour time intervals following the other administrations.

Another common dosing regimen is that in which an individual takes one dose upon awakening and a second dose upon retiring. In this common twice-a-day regimen, sixteen hours may elapse between the daytime dose (6:00 AM to 10:00 PM) and only eight hours (10:00 PM to 6:00 AM) until the next dose is taken upon arising the next morning. Therefore, the individual will have either too high a dose during the night, or too low a dose during the day because the doses are equal.

Currently employed dosage forms, such as the ones described above, are problematic for a number of reasons. First, the administration of equal doses for time intervals of differing lengths results in levels of active therapeutic substance at the site of action which may be alternatively too high or too low to maintain therapeutic effectiveness over a given period of time.

Secondly, the currently employed dosage forms involve the administration of even doses at uneven time intervals thereby failing to account for physiological anomalies which occur throughout the course of a given 24 hour period. For example, conventional dosage forms fail to recognize the difference in an individual's metabolic rate during that individual's sleeping and waking hours.

Thirdly, currently used dosage forms will generally result in the administration of higher amounts of drug to a patient over a given period of time, which will in turn result in increased incidents of side effects. Further, as the body adapts to the presence of the higher amounts of active therapeutic substance, said therapeutic substance will likely be less efficacious.

Fourthly, currently used dosage forms fail to factor into consideration the effects of the varying solubilities of their components. For example, in currently employed drug dosage forms a therapeutic substance containing a water-soluble component and a non water-soluble component would have equal amounts of water-soluble component present in each dose. Therefore, a tablet to be administered just prior to bedtime, for example, would contain the same dose of water-soluble substance as a tablet to be administered in the morning dose. Such a dosing form fails to account for the specific absorption of each component at various times and again may result in levels of active therapeutic substance at the site of action which are either too high or too low at various times throughout a given 24 hour period.

In addition to the importance of the dosage forms for maintaining therapeutically effective drug levels at the site of action, the success of a dosing form in achieving its therapeutic objective is largely dependent upon an individual's compliance with his or her drug dosing regimen. A individual's failure to comply with a dosing regimen, e.g. failure to take one or more doses of a drug or taking too many doses, will have an adverse impact upon the success of the regimen. Individuals may fail to comply with their drug dosing regimen for a number of reasons. For example, drug dosing regimens, such as the 9-1-5-9 regimen described above involve a rigid dosing schedule that may be incompatible with an individual's personal schedule. Such a rigid dosing schedule when combined with normal human traits such as forgetfulness or denial of medical condition, as well as a busy life, represent substantial obstacles to compliance with a drug dosing regimen. Accordingly, such rigid dosing regimens often result in the failure by an individual to take one or more doses at the prescribed time. This has an adverse impact on the levels of the therapeutic substance at the active site and consequently on the overall efficacy of the therapeutic substance.

Methods for optimizing the therapeutic effects of therapeutic substances by improving patient compliance with dosage regimens have been described. York, U.S. Pat. No. 5,521,208, describes novel compositions containing non-racemic mixtures of enantiomers tailored specifically to allow less frequent dosing and thus a more convenient dosing regimen to improve patient compliance of metabolically impaired individuals, such as individuals suffering from diabetes mellitus.

Lieberman et al., U.S. Pat. No. 5,597,072, describe a totally interactive patient compliance method which encourages compliance by a patient with their drug therapy by requiring that the patient call a phone number to obtain a code which will allow the patient to remove their medication from a specially designed dispenser and by recording each such phone call to signal that the patient has complied with the regimen.

Batchelor, U.S. Pat. No. 4,889,238, discloses a medicament package designed to improve compliance with a complex therapeutic regimen by providing blister packs containing the various medications to be administered and arranged in the order of their intended use.

Methods for optimizing the therapeutic effects of drugs by monitoring patients have also been described. Kell, U.S. Pat. Nos. 5,652,146 and 5,547,878, discloses a method of monitoring compliance of a patient that has been placed on a medication maintenance program with prescribed medication by determining a normalized urine medication concentration and comparing same to an expected medication concentration for an average patient.

Baggett, U.S. Pat. No. 4,811,845, discloses a medication compliance procedure and packaging system designed to ensure that a patient receives accurate doses of the required medication at scheduled times. The system involves a package indicating the time when each medication should be taken.

However, the above methods for improving patient compliance and monitoring patient compliance, would not alone optimize the efficacy of therapeutic substances and thus would not compensate for the previously described deficiencies of current drug dosage forms. Moreover, in the vast majority of cases, the above described methods for improving patient compliance or monitoring patients would not be appropriate because they are too costly or time consuming and because they are applicable to only a limited number of specific therapeutic substances, therapies, conditions or situations.

Dividing the total daily dosage of a drug into uneven multiple dosages has been previously described in the medical literature. For example, it has been disclosed that Sinemet®, a medication for treating Parkinson's disease, may be administered three times a day with each of the first two doses containing 300 mg of the medication and the third dose containing 200 mg of the medication. See *Physicians' Desk Reference (PDR)*, Fifty First Edition, 959–963 (1997). Also disclosed in the medical literature is that subsequent to initiating a patient on Dilantin®, a medication for treating epilepsy, "the dosage may be adjusted to suit individual requirements". See *Physicians' Desk Reference (PDR)*, Fifty First Edition, 1965–1970 (1997). The medical literature also discloses that when administering Depakote®, a medication effective in treating migraines, mania or epilepsy, after an initial dosage of 750 mg daily, the dosage should be increased rapidly until the desired clinical effect or plasma concentration is achieved. See *Physicians' Desk Reference (PDR)*, Fifty First Edition, 418–422 (1997).

However, these uneven dosage forms, as described in the medical literature, involve starting doses and arbitrary dose amounts which are not directed to all uses of a standardized dosage form for the purpose of achieving predictable concentrations of active therapeutic substance at a site of action, or plasma concentrations that would be associated with optimal therapy. Further, the uneven dosage forms described in the medical literature are associated with endpoint determinations or adjustments made in response to the clinical effects of the therapy. Moreover, the uneven dosage forms previously described do not recognize that the therapeutic window itself may change throughout the course of a day. For example, a patient may have different therapeutic need during the day than at night.

Another disclosure in the medical literature involves the administration of Ismo®, a medication administered for the prevention of angina pectoris due to coronary artery disease. According to the literature, Ismo® should be administered in two doses a day, only seven hours apart. *Physicians' Desk Reference (PDR)*, Fifty First Edition, 2844–2845 (1997). However, this dosing schedule has been developed to minimize the impact of refractory tolerance and involves the use of equal doses in each administration of the drug.

The need to pattern administration of certain drugs to gradually increase blood level in a short period of time, often called titrating, has been recognized, as exemplified above. When titrating a patient, either a larger dose may be given in periods of the day or night when adverse symptoms climax, or smaller amounts may be given to reduce side effects such as sleeplessness. It is well known, however, that such methods of administration are designed to individualize dosing to each patient and do not deal with subsequent need to establish and maintain steady state. Conventionally, subsequent dosing is done once a day, twice a day, three times a day, four times a day or continuously.

In those instances where the prior art discloses applications of dissimilar doses, it is cited only for use in initially titrating patients and only for a limited number of disease states. The purpose of the prior art methods involving titration are to build plasma levels as quickly as possible. Dissimilar doses are used only incidentally to reach a desirable drug response. (Note, the contrast between "uneven dosing" as used herein in this patent where an a priori blood level has been anticipated based on the exactness of the uneven dose regimen.)

Therefore, there is a need for methods of treatment used not only to establish therapeutic effects, but also to achieve and maintain therapeutic effectiveness in steady state. There is also a need for methods of treatment which have universal applicability (i.e, the ability to be used in conjunction with a vast multitude of therapeutics). Whereas the prior art exists to provide pharmacological convenience and has limited applicability to a relatively short administration period, a need exists for methods useful in continued and prolonged treatment.

Further, a need remains for an easy and economical approach to achieving and maintaining levels of a therapeutic substance known to be associated with optimal therapy and which can be applied to a limitless range of existing and future therapeutic and other substances. More specifically, a need remains for dosage forms, regimens, methods and compositions which account for uneven time intervals between doses, as well as daily physiological anomalies, and which can be administered in a more convenient manner.

Such dosage forms, would be highly desirable in that they would improve compliance with the dosing regimen, while at the same time optimizing the therapeutic effects of the active therapeutic substance being administered. Another desirable aspect of such dosage forms are that they would reduce the overall amount of therapeutic substance or substances administered and therefore minimize incidents of side effects and further optimize therapeutic effects.

SUMMARY OF THE INVENTION

In the case of multiple dosing, it is well known that patients do not space doses evenly, or even follow the same dosing schedule from day to day. Twice a day dosing may be instituted by the patient at 7:00 am and 12:00 pm. The first dose is thus required to provide the desired therapeutic effect for sixteen hours and the second like dose for eight hours. The plasma concentration profile which will result from repeated dosing on a similar schedule is shown in FIG. I which assumes a drug half-life of 12 hours.

The present invention recognizes the inconsistency, inadequacy, and dangers of such conventional dosing and provides flexible means to better assure compliance, maintain more even plasma levels, and reduce incidents of side effects. Generally, average daily requirement of therapeutic substance, as the result of such improved regulation of dosage, is reduced as well.

The present inventive subject matter is based on the discovery that novel, uneven dosage forms provide a more even and predictable physiologic response, or more even and predictable plasma concentrations, over any given period of time than currently employed dosage forms, thus optimizing the effectiveness of said biologically useful substance. The novel dosage forms of the present invention account for the uneven time intervals between doses, as well as daily physiological anomalies, which currently employed dosage forms do not address. Specifically, it is possible using the dosing forms of the present invention to target particular drug levels at different times throughout the day in recognition that different levels of drug may be desirable at different times throughout a day.

The novel dosage forms of the present invention can be administered in a convenient manner to improve patient compliance. Further, the dosage forms can be applied to any biologically active useful substance or substances in any situation. The dosage forms also reduce the overall amount of biologically useful substance required to be administered over a given period of time and therefore minimize incidents of side effects and further optimize therapeutic effects.

The drug delivery regimens of the invention comprise an active therapeutic substance administered during at least one 24 hour period of time to provide effective therapeutic levels of the active therapeutic substance at a site of action in an animal (i.e., human, mammal or any other animal) over said period, wherein each individual dose is independently adjusted to be administered to optimize levels of the active therapeutic substance or substances at the site of action for maximum efficacy, and wherein the dose amount at each administration will be independently determined by the formula $TD(t)=CD(t)+RD(t)$, where t is the time at which the dose is to be administered, TD (therapeutic dose) is the therapeutically effective dose at time (t), CD (current dose) is the dose to be administered at time (t), and RD (residual dose) is the amount of active therapeutic substance remaining from the previous dose administration.

In another embodiment of the invention, a drug delivery regimen comprises multiple doses of an active therapeutic substance administered during at least one 24 hour period of time to provide effective therapeutic levels of the active therapeutic substance at a site of action in an animal over said period, wherein the active therapeutic substance is administered in uneven doses and over varying time intervals, and wherein the uneven doses and the varying time intervals are selected to optimize levels of the active therapeutic substance at the site of action for maximum efficacy.

In yet another embodiment of the invention, a drug delivery regimen comprises multiple doses of an active therapeutic substance administered during at least one 24 hour period of time to provide effective therapeutic levels of the active therapeutic substance at a site of action in an animal over said period, and wherein each dose is independently calculated according to known pharmacokinetic parameters of the active therapeutic substance with variations to account for physiological anomalies which occur during said period to optimize levels of the active therapeutic substance at the site of action for maximum efficacy.

In a further embodiment of the invention, a drug delivery regimen comprises multiple doses of an active therapeutic substance administered during at least one 24 hour period of time to provide effective therapeutic levels of the active therapeutic substance at a site of action in an animal over said period, wherein the time at which each dose is to be administered is tailored to a convenient schedule for the animal, and wherein the dose amount at each administration will be independently determined by the formula $TD(t)=CD(t)+RD(t)$, where t, TD, CD and RD are as defined above.

In a still further embodiment of the invention, a method of enhancing the therapeutic effect of an active therapeutic substance in an animal, comprises:

(a) determining known pharmacokinetic parameters of the active therapeutic substance;

(b) determining a number of doses to be administered during a 24 hour period of time and determining a time at which each dose will be administered by considering both the animal's schedule and physiological anomalies during the 24 hour period; and (c) independently calculating the amount of each dose in accordance with the equation $$TD(t)=CD(t)+RD(t)$$

where t, TD, CD and RD are as defined above.

In yet another further embodiment, pharmaceutical compositions of the invention for optimizing therapeutic activity in an animal comprise a substance consisting essentially of an active therapeutic substance in dose amounts calculated according to the formula $TD(t)=CD(t)+RD(t)$, where t, TD, CD and RD are as defined above with a suitable pharmaceutical carrier.

In another embodiment, a drug delivery regimen of the invention comprises multiple active therapeutic substances administered during at least one 24 hour period of time to provide effective therapeutic levels of the active therapeutic substances at a site of action in an animal over said period, wherein each dose is independently tailored to optimize levels of the respective active therapeutic substances at the site of action for maximum efficacy.

In yet another embodiment of the invention, a drug delivery regimen comprises multiple active therapeutic substances administered over a 24 hour period of time to provide effective therapeutic levels of the respective active therapeutic substances over said period, wherein the ratio of active therapeutic substances to each other for each individual dose will be independently tailored to optimize levels of the active therapeutic substance at the site of action for maximum efficacy.

In a further embodiment of the invention, a drug delivery regimen comprises multiple active therapeutic substances administered over a 24 hour period of time to provide effective therapeutic levels of the active therapeutic substance at a site of action in an animal over said period, wherein the ratio of the therapeutic substances to each other for each dose will not equal the ratio of the therapeutic substance to each other for at least one of the other doses, and wherein the ratio of therapeutic substances to each other for each individual dose is independently tailored to optimize levels of the active therapeutic substance at the site of action for maximum efficacy.

In a still further embodiment of the invention, a drug delivery regimen comprises an active therapeutic substance with a water-soluble phase and a non water-soluble phase administered during at least one 24 hour period of time to provide effective therapeutic levels of the active therapeutic substances at a site of action in an animal over said period, wherein the ratio of water-soluble phase to non water-soluble phase for each dose is independently tailored to optimize levels of the active therapeutic substance at the site of action for maximum efficacy.

In yet another further embodiment of the invention, a drug delivery regimen comprises an active therapeutic substance with a water-soluble phase and a non water-soluble phase administered over a 24 hour period of time to provide effective therapeutic levels of the active therapeutic substance at a site of action in an animal over said period, wherein for each individual dose the ratio of the water-soluble phase to the non water-soluble phase will not equal the ratio of the water-soluble phase to the non water-soluble phase for at least one of the other doses, and wherein the ratio of water-soluble phase to non water-soluble phase for each individual dose will be independently tailored to optimize levels for maximum efficacy.

In another embodiment of the invention, a pharmaceutical composition for optimizing therapeutic activity comprises a substance consisting essentially of multiple active therapeutic substances, wherein the substance has a water-soluble phase and a non water-soluble phase in combination with a suitable pharmaceutical carrier, and wherein the ratio of water-soluble phase to non water-soluble phase is independently tailored to optimize levels of the respective active therapeutic substances at a site of action in an animal for maximum efficacy, and wherein said ratio is determined according to the time at which said composition is to be administered.

Thus, the inventive subject matter optimizes the therapeutic effectiveness of any active therapeutic substance.

BRIEF DESCRIPTION OF THE DRAWINGS

FIG. I shows the expected results of the application of this invention to Methylphenidate administered to treat Attention Deficit Disorder (ADD). See Example I.

FIG. II shows the expected results of the application of this invention to Methylphenidate administered to treat Narcolepsy. See Example II.

FIG. III shows the expected results of the application of this invention to Vitamin $B_{12}$ administered for general health maintenance. See Example III.

FIG. IV shows the expected results of the application of this invention to Benzodiazipine administered to treat Anxiety. See Example IV.

FIG. V shows the expected results of the application of this invention to terazosin hydrochloride, available from Abbott Laboratories under the tradename Hytrin, administered to prevent hypertension and heart attack. See Example V.

FIG. VI shows the expected results of another application of this invention to terazosin hydrochloride, available from Abbott Laboratories under the tradename Hytrin, administered to prevent hypertension and heart attack. See Example VI.

FIG. VII shows the expected results of the application of this invention to verapamil hydrochloride administered to prevent hypertension and heart attack. See Example VII.

FIG. VIII shows the expected results of the application of this invention to Cimetidine administered for the prevention of Gastroesophageal Reflux Disease (GERD). See Example VIII.

FIG. IX shows the expected results of the application of this invention to Cimetidine administered for the treatment of gastric ulcers. See Example IX.

FIG. X shows the expected results of the application of this invention to the diuretic Chlorothiazide Sodium administered for the treatment of hypertension. See Example X.

DETAILED DESCRIPTION OF THE INVENTIONS

Definitions

As used herein, "Animal" refers to a human, mammal or any other animal.

"Drug delivery regimen" refers to the overall way in which a biologically useful substance or active therapeutic substance is administered to an animal.

Both "substance" and "biologically useful substance" refer to any substance or substances comprising a drug, active therapeutic substance, metabolite, medicament, vitamin, or mineral, any substance used for treatment, prevention, diagnosis, cure or mitigation of disease or illness, any substance which affects anatomical structure or physiological function, or any substance which alters the impact of external influences on an animal, or metabolite thereof, and as used herein, encompasses the terms "active substance", "therapeutic substance", "agent", "active agent", "active therapeutic agent", "drug", "medication", "medicine", "medicant", and other such similar terms.

"Site of action" refers to the location at which an active therapeutic substance must be present to have its intended effect, and is synonymous with the term "active site".

"Effective therapeutic levels" refers to a range of levels of active therapeutic substance at a site of action at which said active therapeutic substance will achieve its intended effect.

"Optimize" refers to the attainment of a level that falls within the range of levels at which therapeutically effective levels are achieved with little or no side effects.

"Maximum efficacy" refers to the highest amount of therapeutic effectiveness attainable with a specific active therapeutic substance.

"Therapeutic dose" is the range of levels of therapeutic substance required at the site of action to achieve the intended effect of said therapeutic substance, and is synonymous with the term "therapeutically effective dose".

"Therapeutic window" refers to the range of plasma concentrations, or the range of levels of therapeutically active substance the site of action, with a high probability of therapeutic success.

"Plasma concentration" refers to the concentration of an active therapeutic substance in blood plasma.

"Drug absorption" refers to the process of movement from the site of administration toward the systemic circulation.

"Bioavailability" refers to the rate at which an active moiety (drug or metabolite) enters the general circulation, thereby gaining access to a site of action.

"Chemical (pharmaceutical) equivalence" refers to drug substances that contain the same compound in the same amount and that meet current official standards; however, inactive ingredients in the drug substances may differ.

"Bioequivalence" refers to chemical equivalents that, when administered to the same individual in the same dosage regimen, result in equivalent concentrations of drug in blood and tissues.

"Therapeutic equivalence" refers to two drug substances that, when administered to the same individual in the same dosage regimen, provide essentially the same therapeutic effect or toxicity; they may or may not be bioequivalent.

"Drug Elimination" refers to the sum of the processes of drug loss from the body.

"Metabolism" refers to the process of chemical alteration of drugs in the body.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Half-life" refers to the time required for the plasma drug concentration or the amount in the body to decrease by 50%.

The present invention uses blood level data and clinical observations to show that conventional methods of dosing result in plasma levels which are often inconsistent with therapeutic need. Further, the present invention provides a simple mathematical means to usefully predict results of dosing. This has led to the non-obvious discovery that, by altering dosage forms and dosing regimens, less therapeutic substance can be dosed to provide uniform therapeutic effectiveness or nonuniform effectiveness patterned to physiologic need and reduced incidence of side effects.

The present inventive subject matter recognizes that the administration of equal doses of an active therapeutic substance for time intervals of differing length results in levels of active therapeutic substance at the site of action which are alternatively too high or too low to consistently maintain therapeutic effectiveness over a given period of time. Moreover, a regimen involving the administration of such doses is particularly susceptible to physiological anomalies, such as changes in metabolism, throughout the course of any 24 hour period of time. It has been found that by tailoring each individual dose of an active therapeutic substance to the time interval for which said substance is to be administered and the time of day at which each dose is to be administered, more even therapeutically effective levels of said substance at the site of action, or more even plasma concentrations associated with optimal therapy, are achieved over time. Consequently, by tailoring each individual dose independently of the other doses, improved efficacy, and reduced side effects, are attained relative to currently employed even dosage forms.

It has been unexpectedly discovered that uneven dosing of biologically useful substances will maintain more uniform blood levels and systemic effects when the dosing is patterned to the uneven intervals in which these substances are administered, and the differing time related biochemical needs that may be time related, oftentimes with lower daily doses required because of the sparing effect which can result from such uneven dosing.

Dosing intervals are conventionally QD (once a day), DID (twice a day), TID (three times a day), QID (four times a day) or more frequent. Time of administration is based on half-life, formulation of the dosage form being utilized, systemic reactivity, convenience, whether self administered or regimented, and whether the substance is therapeutic, nutritional, steroidal, or anti-infective.

Unless a substance is controlled released, or has a long half-life permitting QD administration, the time interval between ingestion of doses is ordinarily uneven. For example, if a substance is ingested upon arising and when retiring, the intervals are probably 16 and 8 hours. If taken upon arising, mid-day, and when retiring, intervals may be 5, 11 and 8 hours. If taken evenly spaced during awake hours, intervals might be 5.33, 5.33, 5.33 and 8 hours. In such cases, rational dosing should be uneven to be consistent with uneven time intervals.

Nutritionals and certain drugs, and steroids, antibiotics and like substances may best be taken on a full stomach. Such daytime intervals may be uneven and time between last daytime dose and next morning dose different.

When drugs, nutritionals, antibiotics and other therapeutic substances are administered parenterally (via drip system), therapeutic need and nursing convenience may give rise to intervals of administration that are unevenly spaced. The dose beginning a long period before the next dose is given should be larger than that of a following short period if uniform effects are desired. If it is desirable to establish higher blood levels during a daytime or night-time period, again the dosing should be uneven.

In administrating liquids, parenteral, salves, orifice preparations such as ointment, suspensions and liquids, measuring devices are used which facilitate uneven dosing. In the case of tablets, molded substances, or capsules, the dosage form should be adaptable to uneven dosing. Units having different dose levels can be prepackaged, for example in blister packs, and labeled for time of ingestion. Intervals can be BID, TID, QID or more frequent. In the case of capsules, one or more delayed action pellets can be included with long acting beads. Undoubtedly there are other alternative ways to formulate. As an example, long acting microparticles and suitable amounts of one or more amounts of particles with more delayed action microparticles may be mixed and encapsulated. Matrix substrates can be used to form 2,3, or 4 multilayered tablets or press coated tablets. Press coated tablets can have delayed action cores. Differently formulated multilayered and press coated tablets, which may include coated and uncoated tablets packaged to specify time of use, can be used. Long acting and delayed action microparticles can likewise be suspended in parenteral fluids to provide uneven dosing. The same principle can be applied to ointments and salves which can be blister packed to differentiate doses. The above dosage forms are examples of existing dosage forms that can be adapted to provide uneven dosing and benefit derived therefrom.

Drug Delivery Regimens of the Invention

According to a first aspect of the invention, a drug delivery regimen comprises an active therapeutic substance administered during at least one 24 hour period of time to provide effective therapeutic levels of the active therapeutic substance at a site of action in an animal over said period, wherein each individual dose is independently adjusted to be administered to optimize levels of the active therapeutic substance at the site of action for maximum efficacy, and wherein the dose amount at each administration will be independently determined by the following formula:

$$TD(t) = CD(t) + RD(t)$$

where t is the time at which the dose is to be administered,

TD (therapeutic dose) is the therapeutically effective dose at time (t),

CD (current dose) is the dose to be administered at time (t), and

RD (residual dose) is the amount of active therapeutic substance remaining from the previous dose administration.

The present invention contemplates the use of known pharmacodynamic and pharmacokinetic parameters for active therapeutic substances. The present invention recognizes that the pharmacokinetic behavior of most drugs may be summarized by parameters that relate variables to each other. These p arameters are constants, although their values may differ from patient to patient and in the same patient under different conditions. The basic pharmacokinetic parameters and their defining relationships are shown in Table I below:

TABLE I

| | Relationship | | Parameter | | |
|---|---|---|---|---|---|
| 1. | Absorption | | | | |
| | Rate of absorption | = | Absorption rate constant | × | Amount remaining to be absorbed |
| 2. | Amount Absorbed | = | Bioavailability | × | Dose |
| | Distribution | | | | |
| 3. | Amount in Body | = | Volume of Distribution | × | Plasma drug concentration |
| 4. | Unbound drug in plasma | = | Fraction Unbound | × | Plasma drug Concentration |
| | Elimination | | | | |
| 5. | Rate of elimination | = | Clearance | × | Plasma drug concentration |
| 6. | Rate of renal excretion | = | Renal clearance | × | Plasma drug concentration |
| 7. | Rate of metabolism | = | Metabolic clearance | × | Plasma drug concentration |
| 8. | Rate of renal excretion | = | Fraction excreted unchanged | × | Rate of elimination |
| 9. | Rate of elimination | = | Elimination Rate Constant | × | Amount in body |

Determination of the proper dosage for a particular situation is performed using well known procedures and techniques available to the ordinary skilled artisan. The present invention enables a person skilled in the art to determine the appropriate dosage amounts to satisfy a therapeutic need by incorporating either known pharmacological parameters or readily ascertainable pharmacological parameters for a specific active therapeutic substance.

Moreover, the present invention recognizes that successful drug therapy requires planning drug administration according to the needs of the individual. One traditional approach for achieving successful individualized drug administration involves empirically adjusting the drug dosage until the therapeutic objective is met. However, this approach is frequently inadequate because of delays or undue toxicity. See *The Merck Manual*, Sixteenth Edition, 277:2610 (1992). An alternative approach for achieving individualized administration involves initiating drug administration according to the expected absorption and disposition (distribution and elimination) of the drug in an individual. The expected absorption and disposition of the drug in an individual is determined by using the known pharmacokinetic parameters as a function of the age and weight of the individual. Both of the above methods or any other such methods, without limitation, may be employed in conjunction with the present invention.

The present invention will result in the lowering of overall dosage required for maintaining even therapeutically effective levels of an active therapeutic substance at a site of action over a given time period. This effect is termed the "sparing dosage phenomena". The sparing dosage phenomena is particularly dramatic in the case of active therapeutic substances with a long half-life. One particularly beneficial aspect of the sparing dosage phenomena created by the present invention is that incidents of side effects are minimized and less drug is required to consistently achieve therapeutic levels.

In a preferred embodiment of the invention, the active therapeutic substance is administered to minimize incidents of side effects.

Another beneficial aspect of the present invention is that a drug dosing regimen may be established which is most convenient for the patient. By individually tailoring each dose to the time interval for which it is administered and/or the time of day at which it is administered, less frequent dosing and greater convenience of dosing may be attained. A more convenient dosing schedule will improve patient compliance with the therapy.

It is also possible in the present drug dosage regimens to combine various forms of release, which include, without limitation, extended release, controlled release, timed release, sustained release, delayed release, long acting, and pulsatile delivery, with immediate release to deliver various active therapeutic substances over various rates of release. The ability to obtain extended release, controlled release, timed release, sustained release, delayed release, long acting, pulsatile delivery and immediate release characteristics is performed using well known procedures and techniques available to the ordinary skilled artisan. Each of these specific techniques or procedures does not constitute an inventive aspect of this invention.

The active therapeutic substance may be administered in one or more dosage form(s) consisting of the therapeutic substance or multiple therapeutic substances and other ingredients formulated into a useable substance. Any pharmaceutically acceptable dosage form, and combinations thereof, is contemplated by the invention. Examples of such dosage forms include, without limitation, liquid, solution, suspension, emulsion, tablet, multi-layer tablet, bi-layer tablet, capsule, gelatin capsule, caplet, lozenge, chewable lozenge, bead, powder, granules, dispersible granules, cachets, douche, suppository, cream, topical, inhalant, aerosol inhalant, patch, particle inhalant, implant, depot implant, ingestible, injectable, or infusion. The preparation of any of the above dosage forms is well known to those skilled in the art; all of which are incorporated herein by reference.

The present invention contemplates substances formulated for administration by any route, including without limitation, oral, buccal, sublingual, rectal, parenteral, topical, inhalational, injectable and transdermal. The physicochemical properties of therapeutic substances, their formulations, and the routes of administration are important in absorption. Absorption refers to the process of drug movement from the site of administration toward the systemic circulation. Most orally administered therapeutic substances are in the form of tablets or capsules primarily for convenience, economy, stability, and patient acceptance. They must disintegrate and dissolve before absorption can occur. Using the present invention with any of the above routes of administration or dosage forms is performed using well known procedures and techniques available to the ordinary skilled artisan.

The present invention contemplates the use of pharmaceutically acceptable carriers which may be prepared from a wide range of materials. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches and derivatives, as well as other conventional binders well known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

The plasticizers used in the dissolution modifying system are preferably previously dissolved in an organic solvent and added in solution form. Preferred plasticizers may be selected from the group consisting of diethyl phthalate, diethyl sebacate, triethyl citrate, crotonic acid, propylene glycol, butyl phthalate, dibutyl sebacate, castor oil and mixtures thereof, without limitation. As is evident, the plasticizers may be hydrophobic as well as hydrophilic in nature. Water-insoluble hydrophobic substances, such as diethyl phthalate, diethyl sebacate and castor oil are used to delay the release of water-soluble drugs, such as potassium chloride. In contrast, hydrophilic plasticizers are used when water-insoluble drugs are employed which aid in dissolving the encapsulating film, making channels in the surface, which aid in drug release.

Preferably, the active therapeutic substance is administered in one or more dosage form(s) independently selected from the group consisting of liquid, solution, suspension, emulsion, tablet, bi-layer tablet, capsule, gelatin capsule, caplet, lozenge, chewable lozenge, bead, powder, granules, dispersible granules, cachets, douche, suppository, cream, topical, inhalant, patch, particle inhalant, implant, ingestible, injectable, or infusion.

The dosage forms can be in the form of a bi-layer tablet composed of at least one immediate-release layer. Also, the multi-layer tablet can be coated for ease of administration or can be enteric coated to reduce any gastric irritation and the unpleasant "burping" produced by certain therapeutic substances, such as vitamins and minerals. Also, multi-particulate design of extended release and immediate-release components can be enteric coated and compressed into a tablet or filled into hard or soft gelatin capsules. Further, the substance may be coated for an unlimited variety of effects, such as for delayed release, extended release, timed release, sustained release, and combinations thereof, without limitation.

The dosage forms of the present invention involve the administration of an active therapeutic substance or multiple active therapeutic substances in a single dose during a 24 hour period of time or multiple doses during a 24 hour period of time. The doses may be uneven in that each dose is different from at least one other dose. The present invention contemplates variations between doses to include different quantities of the total dose, different quantities or proportions of an individual therapeutic substance or multiple therapeutic substances within a dose, or different quantities or proportions of a related group of therapeutic substances, such as water-soluble therapeutic substances, within a dose. The time intervals between the administration of each dosage may also be uneven in that the time interval between each dose is different from at least one other such time interval.

The active therapeutic substance may be administered in uneven doses or the active therapeutic substance may be administered at uneven time intervals over the course of a 24 hour period of time. An "uneven dose" contemplates any aspects of the doses which cause them to vary from one to another. Thus, uneven doses may vary as to the quantity of a specific therapeutic substance, as to the ratio of various therapeutic substances, or as to any other element, such as, the manner of release, e.g. controlled release versus immediate release. For example, a patient may be administered an AM dose and a PM dose, wherein the AM dose is larger or smaller than the PM dose. A patient may be administered, an AM dose and a PM dose, wherein the AM dose is for immediate release and the PM dose is administered for controlled release. Another example involves the administration of an AM dose and a PM dose, wherein the AM dose has a higher or lower amount of a water-soluble active therapeutic substance present than that present in the PM dose. An AM dose and a PM dose may be administered, wherein the AM dosage has a higher or lower amount of a non water-soluble drug present than that present in the PM dosage. Further, two PM doses may be administered, wherein the first PM dose is administered immediately after dinner and the second PM dose is administered immediately prior to bedtime.

The dosage may also be adjusted for subsequent 24 hour periods of time. Further, the active therapeutic substance may be substituted for another active therapeutic substance. Adjustments to the dosage and substitutions of therapeutic substances may be done in response to clinical effects or observations, patient complaints, monitoring studies or test results, or for any other reason.

The active therapeutic substance of the invention can vary widely depending upon the desired objective. The active therapeutic substance may be described as a single entity or a combination of entities. Examples of useful active therapeutic substances include, drugs from all major categories, and without limitation, for example, analgesics, such as acetaminophen, ibuprofen, flurbiprofen, ketoprofen, voltaren (U.S. Pat. No. 3,652,762), phenacetin and salicylamide; antiinflammatories selected from the group consisting of naproxen and indomethacin; antihistamines, such as chlorpheniramine maleate, phenindamine tartrate, pyrilamine maleate, doxylamine succinate, phenyltoloxamine citrate, diphenhydramine hydrochloride, promethazine, brompheniraminemaleate, dexbrompheniramine maleate, clemastine fumerate and triprolidine; antitussives selected from the group consisting of dextromethorphan hydrobromide and quiaifenesin; expectorants such a guaifenesin; decongestants, such as phenylephrine hydrochloride, phenylpropanolamine hydrochloride, pseudoephedrine hydrochloride, ephedrine; narcotics, such as morphine, and codeine and their derivatives, such as oxycodone and hydromorphone; antibiotics such as erythromycin, penicillins and cephalosporins and their derivatives; bronchodilators such as theophylline, albuterol and terbutaline; cardiovascular preparations such as diltiazem, propranolol, nifedepine and clonidine; central nervous system drugs such as thioridazine, diazepam, meclizine, ergoloid mesylates, chlorpromazine, carbidopa and levodopa; metal salts such as potassium chloride, and lithium carbonate; minerals selected from the group consisting or iron, chromium, molybdenum and potassium, and vitamins selected from water-soluble vitamins such as B complex, vitamin C, vitamin $B_{12}$ and folic acid.

Particularly preferred dosage forms involve the use of an active therapeutic substance selected from the group consisting of Sinemet(r), levodopa, carbidopa, Eldepryl(r), selegiline, and combinations thereof; Ritalin(r), methylphenidate, and combinations thereof; nitroglycerin, disopyramide, nifedipine, and combinations thereof; antitussives, decongestants, and combinations thereof.

The present invention may be used to treat, cure, prevent, control or alleviate a wide range of conditions and symptoms. For example, the drug delivery regimen of the present invention is administered to treat a condition selected from the group consisting of vitamin and/or mineral deficiency, Parkinson's Disease, Attention Deficit Disorder, Cardiovascular Disorder, Cold/Flu Symptoms, Pain, Childhood Bronchial Asthma, Peptic Ulcer, Post-operative Recuperation, and so forth.

The present invention may also be used for improving overall health and in nutritional supplementation. The present invention may be used with any vitamin and/or mineral supplements, for example, vitamin and mineral supplements tailored to specific life stages and genders, such as vitamin and mineral supplements for pregnant, lactating, non-lactating or menopausal women.

The drug delivery regimens contemplate that each individual dose may be predetermined and therefore independently adjusted without regard for endpoint determinations. In a particularly preferred embodiment of the invention, each individual dose is independently adjusted without regard for an endpoint determination.

Preferably, the drug delivery regimen comprises multiple doses of an active therapeutic substance administered during at least one 24 hour period of time to provide effective therapeutic levels of the active therapeutic substance at a site of action in an animal over said period, wherein the active therapeutic substance is administered in uneven doses and over varying time intervals, and wherein the uneven doses and the varying time intervals are selected to optimize levels of the active therapeutic substance at the site of action for maximum efficacy.

More preferably, the drug delivery regimen comprises multiple doses of an active therapeutic substance administered during at least one 24 hour period of time to provide effective therapeutic levels of the active therapeutic substance at a site of action in an animal over said period, and wherein each dose is independently calculated according to known pharmacokinetic parameters of the active therapeutic substance with variations to account for physiological anomalies which occur during said period to optimize levels of the active therapeutic substance at the site of action for maximum efficacy.

Even more preferably, the drug delivery regimen comprises multiple doses of an active therapeutic substance administered during at least one 24 hour period of time to provide effective therapeutic levels of the active therapeutic substance at a site of action in an animal over said period, wherein the time at which each dose is to be administered is tailored to a convenient schedule for the animal, and wherein the dose amount at each administration will be independently determined by the formula $TD(t)=CD(t)+RD(t)$, where t, TD, CD and RD are as defined above.

Most preferably, the drug delivery regimen of the invention comprises multiple active therapeutic substances administered during at least one 24 hour period of time to provide effective therapeutic levels of the active therapeutic substances at a site of action in an animal over said period, wherein each dose is independently tailored to optimize levels of the respective active therapeutic substances at the site of action for maximum efficacy.

Another aspect of the present invention recognizes that certain types of therapeutic substances exhibit different pharmacodynamic and pharmacokinetic characteristics than others at various times during a 24 hour period of time. For example, it is known that water-soluble B vitamins are used in nervous tissue regeneration, which occurs mainly during sleep. A high morning dose of the water soluble B group of vitamins is excreted rapidly, before having any effect. The present invention accounts for these time sensitive characteristics by varying the proportion of the substances from dose to dose when appropriate. Therefore, in accordance with the present invention, one would divide the B vitamin dose so that a much smaller quantity of B vitamin is present in the A.M. as compared to a much larger quantity in the P.M. This represents a departure from currently employed dosage forms which contain substances in the same proportion from dose to dose.

Preferably, the drug delivery regimen comprises multiple active therapeutic substances administered over a 24 hour period of time to provide effective therapeutic levels of the respective active therapeutic substances over said period, wherein the ratio of active therapeutic substances to each other for each individual dose will be independently tailored to optimize levels of the active therapeutic substance at the site of action for maximum efficacy.

More preferably, the drug delivery regimen comprises multiple active therapeutic substances administered over a 24 hour period of time to provide effective therapeutic levels of the active therapeutic substance at a site of action in an animal over said period, wherein the ratio of the therapeutic substances to each other for each dose will not equal the ratio of the therapeutic substance to each other for at least one of the other doses, and wherein the ratio of therapeutic substances to each other for each individual dose is independently tailored to optimize levels of the active therapeutic substance at the site of action for maximum efficacy.

Even more preferably, the drug delivery regimen comprises an active therapeutic substance with a water-soluble phase and a non water-soluble phase administered during at least one 24 hour period of time to provide effective therapeutic levels of the active therapeutic substances at a site of action in an animal over said period, wherein the ratio of water-soluble phase to non water-soluble phase for each dose is independently tailored to optimize levels of the active therapeutic substance at the site of action for maximum efficacy.

Most preferably, the drug delivery regimen comprises an active therapeutic substance with a water-soluble phase and a non water-soluble phase administered over a 24 hour period of time to provide effective therapeutic levels of the active therapeutic substance at a site of action in an animal over said period, wherein for each individual dose the ratio of the water-soluble phase to the non water-soluble phase will not equal the ratio of the water-soluble phase to the non water-soluble phase for at least one of the other doses, and wherein the ratio of water-soluble phase to non water-soluble phase for each individual dose will be independently tailored to optimize levels for maximum efficacy.

Administration of the active therapeutic substance includes, without limitation, administration of the active therapeutic substance by the individual to whom said substance is being administered (i.e. self-administration), administration by a medical professional to a patient, or administration by any party assisting another party with the taking of said substance (i.e., a parent administering medication to his or her child or a family member administering medication to an elderly relative).

As described above, the present invention encompasses several different inventive means which are all achieved using the methodology set forth herein. For example, one inventive means assures compliance to dosing regimens by providing dosage forms so formulated that a majority of therapeutic substances, heretofore administered twice a day, three times a day, or four times a day, can be ingested upon arising and when retiring; the most convenient and most easily remembered times in a twenty four hour day. Another inventive means involves formulating and administering the therapeutic substances to provide more uniform therapeutic effects when ingested in unequal amounts and uneven intervals, as well as the formulating and administering of therapeutic substances to provide non-uniform therapeutic effects when ingested in equal or unequal intervals to satisfy unequal needs.

The present invention also encompasses the formulating and administering of therapeutic substances, conventionally dosed once a day, in more than one dose to obtain more or less uniform blood concentrations patterned to uniform or non-uniform need and requires less total daily dosage which reduces possible incidence of side effects. Also encompassed by the present invention is the formulating and administering of therapeutic one or more therapeutic substance twice, three times, or four times and day at other intervals than conventional intervals to obtain more optimal blood concentrations and consequent effectiveness.

Although the dosage forms of the invention are preferably intended for humans, it will be understood that said dosage forms may also be utilized in veterinary therapies for other animals.

Methods of the Invention

Another aspect of the present invention is a method of enhancing the therapeutic effect of an active therapeutic substance in an animal, which comprises:

(a) determining known pharmacokinetic parameters of the active therapeutic substance;

(b) determining a number of doses to be administered during a 24 hour period of time and determining a time at which each dose will be administered by considering both the animal's schedule and physiological anomalies during the 24 hour period; and (c) independently calculating the amount of each dose in accordance with the equation $$TD(t) = CD(t) + RD(t)$$

where t, TD, CD and RD are as defined above.

Determination of the proper dosage for a particular situation is performed using well known procedures and techniques available to the ordinary skilled artisan. The present invention enables a person skilled in the art to determine the appropriate dosage amounts for a particular situation by incorporating either known biologic responses, pharmacological parameters or readily ascertainable pharmacological parameters for a specific active therapeutic substance.

Steps (a) and (b) can be performed by the ordinary skilled artisan using information readily available from medical literature or readily determinable using techniques available to the ordinary skilled artisan. The calculation in step (c) can be performed by the ordinary skilled artisan using the information gathered for steps (a) and (b) and using the known relationships between pharmacokinetic parameters. The precise calculations to be used will vary widely depending upon the situation and active therapeutic substance or substances involved.

Compositions of the Invention

Another aspect of the invention includes compositions for optimizing therapeutic activity in an animal, which comprise: a substance consisting essentially of an active therapeutic substance in dose amounts calculated according to the formula $TD(t) = CD(t) + RD(t)$, where t, TD, CD and RD are as defined above in combination with a suitable pharmaceutical carrier.

Determination of the proper dosage for a specific composition is performed using well known procedures and techniques available to the ordinary skilled artisan. The present invention enables a person skilled in the art to determine the appropriate dosage amounts for a particular situation by incorporating either known pharmacological parameters or readily ascertainable pharmacological parameters for a specific active therapeutic substance.

Moreover, the present invention recognizes that successful drug therapy requires planning drug administration according to the needs of each individual. One traditional approach for achieving successful individualized drug administration involves empirically adjusting the drug dosage until the therapeutic objective is met. However, this approach is frequently inadequate because of delays or undue toxicity. See Merck Index, Chapter 277, p. 2610. An alternative approach for achieving individualized administration involves initiating drug administration according to the expected absorption and disposition (distribution and elimination) of the drug in an individual. The expected absorption and disposition of the drug in an individual is determined by using the known pharmacokinetic parameters as a function of the age and weight of the individual. Both of the above methods or any other such methods, without limitation, may be employed in conjunction with the present invention.

Another aspect of the present invention recognizes that certain types of therapeutic substances exhibit different pharmacodynamic and pharmacokinetic characteristics than others at various times during a 24 hour period of time. For example, it is known that water-soluble B vitamins are used in nervous tissue regeneration, which occurs mainly during sleep. A high morning dose of the water soluble B group of vitamins is excreted rapidly, before having any effect. The present invention accounts for these time sensitive characteristics by varying the proportion of the substances from dose to dose when appropriate. Therefore, in accordance with the present invention, one would divide the B vitamin dose so that a smaller quantity of B vitamin is present in the A.M. as compared to a larger quantity in the P.M. This represents a departure from currently employed dosage forms which contain substances in the same proportion from dose to dose.

In a particularly preferred embodiment of the invention, a pharmaceutical composition for optimizing therapeutic activity comprises a substance consisting essentially of multiple active therapeutic substances, wherein the substance has a water-soluble phase and a non water-soluble phase in combination with a suitable pharmaceutical carrier, and wherein the ratio of water-soluble phase to non water-soluble phase is independently tailored to optimize levels of the respective active therapeutic substances at a site of action in an animal for maximum efficacy, and wherein said ratio is determined according to the time at which said composition is to be administered.

The present invention is further illustrated by the following specific examples which are not deemed to be limiting thereof. All amounts specified in the application are based on milligrams unless otherwise indicated. The term "I.U." represents International Units. All percentages used throughout the specification and claims are based on the weight of the final product, unless otherwise indicated, and all formulations total 100% by weight.

An inexhaustible number of examples could be given to support all the ways uneven dosing can be utilized to improve the effectiveness of ingested substances. Nevertheless, the principles by which dosage and form are designed is always the same. To illustrate, the following figures show dose formation and effectiveness of QD, BID, TID and QID drugs, with expected half-lives, converted to uneven form for administration upon awakening and when retiring. For manufacturing a dispensing convenience, it is assumed tablets are used and two tablets are taken upon arising and one when retiring. Because of the sparing effect, a daily dose lower than the conventional daily dose is evaluated in some examples. A QD substance with too short a shelf life to use BID was selected to demonstrate the solution to such a limitation. In such a case, QID drug is developed into a reduced dose relatively short duration long acting form and administered 2 to 1.

EXAMPLES

Example I

The plasma profile for Methylphenidate, available from CibaGeneva under the tradename Ritalin®, when administered in a conventional form, 10 mg at 7:00 am and 10 mg at 12:00 pm, for the treatment of Attention Deficit Disorder (ADD) was determined based on data available in the medical literature and is illustrated by the solid line in FIG. I. Note that when using the conventional administration, high dosages of the drug would be present in the body throughout the afternoon and early evening, causing overstimulation of the patient and resultant side effects, such as twitching and convulsions.

A single dose of 20 mg Ritalin® was then administered to each of 6 normal adult males. After measuring plasma concentrations of the 6 normal adult males, an exemplary plasma profile for the drug, using uneven dosing, 14 mg at 7:00 am and 6 mg at 3:00 pm, was developed with a pharmacokinetic mathematical model, as illustrated by the dashed line in FIG. I. Note that the uneven dosing will result in more acceptable dosages of drug throughout the afternoon and early evening, thus avoiding side effects, while also providing higher dosages of drug in the morning, when the patient is most active and thus most susceptible to the symptoms of ADD.

Example II

The plasma profile for Methylphenidate, available from CibaGeneva under the tradename Ritalin®, when administered in a conventional form, with 10 mg at 7:00 am, 10 mg at 12:00 pm and 10 mg at 5:00 pm, for the treatment of Narcolepsy was determined based on data available in the medical literature and is illustrated by the solid line in FIG. II. Note that when using the conventional administration, lower dosages of the drug are present in the patient during the morning hours when the patient has the greatest difficulty staying awake and increasingly higher dosages of the drug would be present in the body throughout the evening and bedtime hours, resulting in sleeplessness.

A single dose of 20 mg Ritalin® was then administered to each of 6 normal adult males. After measuring plasma concentrations of the 6 normal adult males, an exemplary plasma profile for the drug was developed with a pharmacokinetic mathematical model, using uneven dosing, 20 mg at 7 am and 10 mg at 3:00 pm, as illustrated by the dashed line in FIG. II. Note that the uneven dosing will result in higher levels of the drug in the patient during the morning hours, when the patient needs stimulation the most. Further, the uneven dosing will result in lower levels of drug in the evening and night, thus avoiding the sleeplessness that results from conventional dosing.

Example III

The plasma profile for Vitamin $B_{12}$, when administered in conventional form, 12 mcg at 7:00 am, is illustrated by the solid line in FIG. III. Note that when using the conventional administration, there is virtually no Vitamin $B_{12}$ present in the patient during the evening and nighttime hours when nerve tissue repair, which is known to require Vitamin $B_{12}$, predominantly occurs.

An exemplary plasma profile for Vitamin $B_{12}$ is set forth using uneven dosing, 4 mcg at 7:00 am and 8 mcg at 11 pm, as illustrated by the dashed line in FIG. III. Note that the uneven dosing will result in the presence of high levels of Vitamin $B_{12}$ in the patient during the nighttime hours, when the vitamin is most beneficial to the patient because it is available to assist in the repair of nerve tissue.

Example IV

The plasma profile for Benzodiazipine, available from Roche Products under the tradename Valium®, when administered in a conventional form, 10 mg at 7:00 am, 10 mg at 3:00 pm and 10 mg at 7:00 pm, for the treatment of anxiety, is illustrated by the solid line in FIG. IV. Note that when using the conventional administration, relatively low dosages of the drug are present in patients during the morning hours, when patients are most likely to experience the most severe symptoms of anxiety. Further, when using conventional administration, relatively high dosages of the drug are present during the nighttime hours when the symptoms of anxiety tend to be minimal.

An exemplary plasma profile for the same drug is set forth using uneven dosing, 20 mg at 7:00 am and 10 mg at 10 pm, as illustrated by the dashed line in FIG. IV. Note that the uneven dosing will result in relatively high levels of the drug in the patient during the morning hours, when symptoms tend to be most severe, and relatively low levels of the drug during the night when the symptoms tend to be least severe.

Example V

The plasma profile for terazosin hydrochloride, available from Abbott Laboratories under the tradename Hytrin®, when administered in a conventional form, with even doses at 7:00 am and 7:00 pm, for the prevention of hypertension and heart attack, is illustrated by the solid line in FIG. V. Note that when using the conventional administration, unnecessarily high dosages of the drug are present in patients during the evening hours, when patients are least likely to experience a heart attack, and during the morning hours when most heart attacks occur, the dosage is lower than may be required.

An exemplary plasma profile for the same drug is set forth using uneven dosing, with two thirds of the total daily dosage administered at 7:00 am and one third of the total daily dosage administered at 10 pm, as illustrated by the dashed line in FIG. V. Note that the uneven dosing will result in relatively high levels of the drug in the patient during the morning hours, when the patient is most vulnerable to a heart attack, and relatively low levels of the drug during the evening when the patient is least vulnerable to a heart attack.

Example VI

The plasma profile for terazosin hydrochloride, available from Abbott Laboratories under the tradename Hytrin®, when administered in a conventional form, with even doses at 7:00 am and 11:00 pm, for the prevention of hypertension and heart attack, is illustrated by the solid line in FIG. VI. Note that when using the conventional administration, unnecessarily high dosages of the drug are present in patients during the evening hours, when patients are least likely to experience a heart attack, and during the morning hours when most heart attacks occur, the dosage is lower than may be required.

An exemplary plasma profile for the same drug is set forth using uneven dosing, with two thirds of the total daily dosage administered at 7:00 am and one third of the total daily dosage administered at 11:00 pm, as illustrated by the dashed line in FIG. VI. Note that the uneven dosing will result in relatively high levels of the drug in the patient during the morning hours, when the patient is most vulnerable to a heart attack, and relatively low levels of the drug during the evening when the patient is least vulnerable to a heart attack.

Example VII

The plasma profile for verapamil, when administered in a conventional form, QD at 11:00 pm, for the treatment and prevention of hypertension, is illustrated by the solid line in FIG. VII. Note that when using the conventional administration, sub-therapeutic levels of the drug are present in patients during a large portion of the day.

An exemplary plasma profile for the same drug is set forth using uneven dosing, with two thirds of the total daily dosage administered at 7:00 am and one third of the total daily dosage administered at 11:00 pm, as illustrated by the dashed line in FIG. VII. Note that the uneven dosing will result in more even levels of the drug throughout the day.

Example VIII

The plasma profile for cimetidine, when administered in a conventional form, 300 mg at 7:00 am and 300 mg at 11:00 pm, for the prevention of Gastroesophageal Reflux Disease (GERD), is illustrated by the solid line in FIG. VIII. Note that when using the conventional administration, unnecessarily high dosages of the drug are present in patients during the morning hours, when patients are least likely to experience symptoms of GERD.

An exemplary plasma profile for the same drug is set forth using uneven dosing, 200 mg at 3:00 pm and 400 mg at 11:00 pm, as illustrated by the dashed line in FIG. VIII. Note that the uneven dosing will result in relatively low, yet adequate levels of the drug in the patient during the morning hours, when the patient is least vulnerable to the symptoms of GERD, and relatively high levels of the drug during the night when the patient is most vulnerable to the symptoms of GERD.

Example IX

The plasma profile for cimetidine, when administered in a conventional form, 300 mg at 7:00 am and 300 mg at 11:00 pm, for the treatment of gastric ulcers, is illustrated by the solid line in FIG. IX. Note that when using the conventional administration, relatively low dosages of the drug are present in patients during the morning hours, when patients are most likely to experience symptoms associated with gastric ulcers.

An exemplary plasma profile for the same drug is set forth using uneven dosing, 200 mg at 7:00 am and 400 mg at 11:00 pm, as illustrated by the dashed line in FIG. IX. Note that the uneven dosing will result in relatively high levels of the drug in the patient during the morning hours, when the patient is most vulnerable to the symptoms associated with gastric ulcers, and relatively low levels of the drug during the night when the patient is least vulnerable to symptoms associated with gastric ulcers.

Example X

The plasma profile for the diuretic chlorothiazide sodium, when administered in a conventional form, 25 mg at 7:00 am and 25 mg at 7:00 pm, for the treatment of hypertension, is illustrated by the solid line in FIG. X. Note that when using the conventional administration, relatively low dosages of the drug are present in patients during the daylight hours, when patients are most vulnerable to hypertension. Further, when using conventional administration, unnecessarily high dosages of the drug are present in patients during night when the patient is less vulnerable to hypertension and when the production of excess urine caused by the drug will disrupt sleep and cause the greatest degree of discomfort and inconvenience.

An exemplary plasma profile for the same drug is set forth using uneven dosing, 42 mg at 7:00 am and 8 mg at 5:00 pm, as illustrated by the dashed line in FIG. X. Note that the uneven dosing will result in relatively high levels of the drug in the patient during the daylight hours, when the patient is most vulnerable to hypertension, and relatively low levels of the drug during the night when the patient is least vulnerable to hypertension and most vulnerable to disruption of sleep and discomfort caused by the production of excessive urine.

The invention being thus described, it will be apparent that the same may be varied in many ways. Such variations are not to be regarded as a departure from the spirit and scope of the invention, and all such modifications are intended to be within the scope of the appended claims.

We claim:

1. A drug delivery regimen, which comprises: an active therapeutic substance administered during at least one 24 hour period of time to provide effective therapeutic levels of the active therapeutic substance at a site of action in an animal over said period, wherein each individual dose is independently adjusted to be administered to optimize levels of the active therapeutic substance at the site of action for maximum efficacy, and wherein the dose amount at each administration is independently predetermined at commencement of said period by the formula $TD(t)=CD(t)+RD$ (t), where t is the time at which the dose is to be administered, TD is the therapeutically effective dose at time (t), CD is the dose to be administered at time (t), and RD is the amount of active therapeutic substance remaining from the previous dose administration; wherein the time at which each dose to be administered is tailored to a convenient schedule for said animal.

2. The drug delivery regimen of claim 1, wherein the active therapeutic substance is administered to minimize incidents of side effects.

3. The drug delivery regimen of claim 1, wherein the active therapeutic substance is administered to improve patient compliance with the drug delivery regimen.

4. A pharmaceutical composition for optimizing therapeutic activity, which comprises:

a substance consisting essentially of multiple active therapeutic substances, wherein the substance has a water-soluble phase and a non water-soluble phase, and wherein the ratio of water-soluble phase to non water-soluble phase is independently tailored to optimize levels of the respective active therapeutic substances at a site of action in an animal for maximum efficacy, and wherein said ratio is determined according to the time at which said composition is to be administered with a suitable pharmaceutical carrier.

5. The drug delivery regimen of claim 1, wherein the active therapeutic substance is administered at least once and may be administered as Immediate Release, Sustained Release, Controlled Release, Delayed Release, Timed Release, Extended Release, or any combination thereof.

6. The drug delivery regimen of claim 5, wherein the active therapeutic substance is administered by pulsatile delivery of the active therapeutic substance.

7. The drug delivery regimen of claim 1, wherein the active therapeutic substance is administered in one or more dosage form(s) independently selected from the group consisting of liquid, solution, suspension, emulsion, tablet, multi-layer tablet, capsule, gelatin capsule, caplet, lozenge, chewable lozenge, bead, powder, granules, dispersible granules, cachets, douche, suppository, cream, topical, inhalant, patch, particle inhalant, implant, ingestible, injectable, or infusion.

8. The drug delivery regimen of claim 1, wherein the active therapeutic substance is administered in one or more dosage form(s) independently selected from the group consisting of tablet, multi-layer tablet, capsule, or caplet.

9. The drug delivery regimen of claim 8, wherein the multi-layer tablet is composed of an extended-release layer and an immediate release layer.

10. The drug delivery regimen of claim 8, wherein the dosage form is coated for ease of administration, coated for delayed release or enteric coated to reduce gastric irritation.

11. The drug delivery regimen of claim 8, wherein the dosage form is enteric coated and compressed into a tablet or filled into hard or soft gelatin capsules.

12. A drug delivery regimen, which comprises: an active therapeutic substance administered during at least one 24 hour period of time to provide effective therapeutic levels of the active therapeutic substance at a site of action in an animal over said period, wherein each individual dose is independently adjusted to be administered to optimize levels of the active therapeutic substance at the site of action for maximum efficacy, and wherein the dose amount at each administration is independently predetermined at commencement of said period by the formula $TD(t)=CD(t)+RD(t)$, where t is the time at which the dose is to be administered, TD is the therapeutically effective dose at time (t), CD is the dose to be administered at time (t), and RD is the amount of active therapeutic substance remaining from the previous dose administration; wherein the time at which each dose to be administered is tailored to a convenient schedule for said animal; and wherein the active therapeutic substance is administered in uneven doses.

13. A drug delivery regimen, which comprises: an active therapeutic substance administered during at least one 24 hour period of time to provide effective therapeutic levels of the active therapeutic substance at a site of action in an animal over said period, wherein each individual dose is independently adjusted to be administered to optimize levels of the active therapeutic substance at the site of action for maximum efficacy, and wherein the dose amount at each administration is independently predetermined at commencement of said period by the formula $TD(t)=CD(t)+RD(t)$, where t is the time at which the dose is to be administered, TD is the therapeutically effective dose at time (t), CD is the dose to be administered at time (t) and RD is the amount of active therapeutic substance remaining from the previous dose administration; wherein the time at which each dose to be administered is tailored to a convenient schedule for said animal; and wherein the active therapeutic substance is administered in uneven doses and at uneven time intervals over the course of the 24 hour period.

14. The drug delivery regimen of claim 1, wherein an AM dose and a PM dose are administered, and wherein the AM dose is larger or smaller than the PM dose.

15. The drug delivery regimen of claim 1, wherein an AM dose and a PM dose are administered, and wherein the AM dose has a higher or lower amount of a water-soluble active therapeutic substance present than that present in the PM dose.

16. The drug delivery regimen of claim 1, wherein an AM dose and a PM dose are administered, and wherein the AM dosage has a higher or lower amount of a non water-soluble drug present than that present in the PM dosage.

17. The drug delivery regimen of claim 1, wherein the dosage is adjusted for subsequent 24 hour periods of time.

18. The drug delivery regimen of claim 1, wherein the active therapeutic substance is substituted for another active therapeutic substance.

19. The drug delivery regimen of claim 1, wherein two PM doses are administered, and wherein the first PM dose is administered immediately after dinner and the second PM dose is administered immediately prior to bedtime.

20. A drug delivery regimen, which comprises: multiple doses of an active therapeutic substance administered during at least one 24 hour period of time to provide effective therapeutic levels of the active therapeutic substance at a site of action in an animal over said period, wherein the active therapeutic substance is administered in uneven doses and over varying time intervals, and wherein the uneven doses and the varying time intervals are selected to optimize levels of the active therapeutic substance at the site of action for maximum efficacy.

21. The drug delivery regimen of claim 20, wherein the active therapeutic substance is administered to minimize incidents of side effects.

22. The drug delivery regimen of claim 20, wherein the active therapeutic substance is administered to improve patient compliance with the drug delivery regimen.

23. The drug delivery regimen of claim 20, wherein the active therapeutic substance is administered to improve convenience of administration.

24. The drug delivery regimen of claim 20, wherein the active therapeutic substance is administered at least once and may be administered as Immediate Release, Sustained Release, Controlled Release, Delayed Release, Timed Release, Extended Release, or any combination thereof.

25. The drug delivery regimen of claim 24, wherein the active therapeutic substance is administered by pulsatile delivery of the active therapeutic substance.

26. The drug delivery regimen of claim 20, wherein the active therapeutic substance is administered in one or more dosage form(s) independently selected from the group consisting of liquid, solution, suspension, emulsion, tablet, multi-layer tablet, capsule, gelatin capsule, caplet, lozenge, chewable lozenge, bead, powder, granules, dispersible granules, cachets, douche, suppository, cream, topical, inhalant, patch, particle inhalant, implant, ingestible, injectable, or infusion.

27. The drug delivery regimen of claim 20, wherein the active therapeutic substance is administered in one or more dosage form(s) independently selected from the group consisting of tablet, multi-layer tablet, capsule, or caplet.

28. The drug delivery regimen of claim 27, wherein the multi-layer tablet is composed of an extended-release layer and an immediate release layer.

29. The drug delivery regimen of claim 27, wherein the dosage form is coated for ease of administration, coated for delayed release or enteric coated to reduce gastric irritation.

30. The drug delivery regimen of claim 27, wherein the dosage form is enteric coated and compressed into a tablet or filled into hard or soft gelatin capsules.

31. The drug delivery regimen of claim 20, wherein the active therapeutic substance is administered in uneven doses.

32. The drug delivery regimen of claim 20, wherein the active therapeutic substance is administered at uneven time intervals over the course of the 24 hour period.

33. The drug delivery regimen of claim 20, wherein an AM dose and a PM dose are administered, and wherein the AM dose is larger or smaller than the PM dose.

34. The drug delivery regimen of claim 20, wherein an AM dose and a PM dose are administered, and wherein the AM dose has a higher or lower amount of a water-soluble active therapeutic substance present than that present in the PM dose.

35. The drug delivery regimen of claim 20, wherein an AM dose and a PM dose are administered, and wherein the AM dosage has a higher or lower amount of a non water-soluble drug present than that present in the PM dosage.

36. The drug delivery regimen of claim 20, wherein the dosage is adjusted for subsequent 24 hour periods of time.

37. The drug delivery regimen of claim 20, wherein the active therapeutic substance is substituted for another active therapeutic substance.

38. The drug delivery regimen of claim 20, wherein two PM doses are administered, and wherein the first PM dose is administered immediately after dinner and the second PM dose is administered immediately prior to bedtime.

39. A drug delivery regimen, which comprises: multiple doses of an active therapeutic substance administered during at least one 24 hour period of time to provide effective therapeutic levels of the active therapeutic substance at a site of action in an animal over said period, and wherein each dose is independently calculated according to known pharmacokinetic parameters of the active therapeutic substance with variations to account for physiological anomalies which occur during said period to optimize levels of the active therapeutic substance at the site of action for maximum efficacy.

40. A drug delivery regimen, which comprises: multiple doses of an active therapeutic substance administered during at least one 24 hour period of time to provide effective therapeutic levels of the active therapeutic substance at a site of action in an animal over said period, wherein the time at which each dose is to be administered is tailored to a convenient schedule for the animal, and wherein the dose amount at each administration is independently predetermined at commencement of said period by the formula $TD(t)=CD(t)+RD(t)$, where t is the time at which the dose is to be administered, TD (therapeutic dose) is the therapeutically effective dose at time (t), CD (current dose) is the dose to be administered at time (t), and RD (residual dose) is the amount of active therapeutic substance remaining from the previous dose administration; wherein the time at which each dose is to be administered is tailored to a convenient schedule for said animal.

41. A method of enhancing the therapeutic effect of an active therapeutic substance in an animal, which comprises:
 (a) determining known pharmacokinetic parameters of the active therapeutic substance;
 (b) determining a number of doses to be administered during a 24 hour period of time and determining a time at which each dose will be administered by considering both the animal's schedule and physiological anomalies during the 24 hour period; and
 (c) independently calculating the amount of each dose in accordance with the equation $$TD(t)=CD(t)+RD(t)$$

where t is the time at which the dose is to be administered, TD (therapeutic dose) is the therapeutically effective dose at time (t), CD (current dose) is the dose to be administered at time (t), RD (residual dose) is the amount of active therapeutic substance remaining from the previous dose administration.

42. The method of claim 41, wherein the active therapeutic substance is administered to minimize incidents of side effects.

43. The method of claim 41, wherein the active therapeutic substance is administered to improve patient compliance with the drug delivery regimen.

44. The method of claim 41, wherein the active therapeutic substance is administered to improve convenience of administration.

45. The method of claim 41, wherein the active therapeutic substance is administered at least once and may be administered as Immediate Release, Sustained Release, Controlled Release, Delayed Release, Timed Release, Extended Release, or any combination thereof.

46. The method of claim 45, wherein the active therapeutic substance is administered by pulsatile delivery of the active therapeutic substance.

47. The method of claim 41, wherein the active therapeutic substance is administered in one or more dosage form(s) independently selected from the group consisting of liquid, solution, suspension, emulsion, tablet, multi-layer tablet, capsule, gelatin capsule, caplet, lozenge, chewable lozenge, bead, powder, granules, dispersible granules, cachets, douche, suppository, cream, topical, inhalant, patch, particle inhalant, implant, ingestible, injectable, or infusion.

48. The method of claim 41, wherein the active therapeutic substance is administered in one or more dosage form(s) independently selected from the group consisting of tablet, multi-layer tablet, capsule, or caplet.

49. The method of claim 48, wherein the multi-layer tablet is composed of an extended-release layer and an immediate release layer.

50. The method of claim 48, wherein the dosage form is coated for ease of administration, coated for delayed release or enteric coated to reduce gastric irritation.

51. The method of claim 48, wherein the dosage form is enteric coated and compressed into a tablet or filled into hard or soft gelatin capsules.

52. The method of claim 41, wherein the active therapeutic substance is administered in uneven doses.

53. The method of claim 41, wherein the active therapeutic substance is administered at uneven time intervals over the course of the 24 hour period.

54. The method of claim 41, wherein an AM dose and a PM dose are administered, and wherein the AM dose is larger or smaller than the PM dose.

55. The method of claim 41, wherein an AM dose and a PM dose are administered, and wherein the AM dose has a higher or lower amount of a water-soluble active therapeutic substance present than that present in the PM dose.

56. The method of claim 41, wherein an AM dose and a PM dose are administered, and wherein the AM dosage has a higher or lower amount of a non water-soluble drug present than that present in the PM dosage.

57. The method of claim 41, wherein the dosage is adjusted for subsequent 24 hour periods of time.

58. The method of claim 41, wherein the active therapeutic substance is substituted for another active therapeutic substance.

59. The method of claim 41, wherein two PM doses are administered, and wherein the first PM dose is administered immediately after dinner and the second PM dose is administered immediately prior to bedtime.

60. A pharmaceutical composition for optimizing therapeutic activity in an animal, which comprises: a substance consisting essentially of an active therapeutic substance in dose amounts calculated according to the formula $TD(t) = CD(t) + RD(t)$, where t is the time at which the dose is to be administered, TD (therapeutic dose) is the therapeutically effective dose at time (t), CD (current dose) is the dose to be administered at time (t), and RD (residual dose) is the amount of active therapeutic substance remaining from the previous dose administration; and suitable pharmaceutical carrier.

61. A drug delivery regimen, which comprises: multiple active therapeutic substances administered during at least one 24 hour period of time to provide effective therapeutic levels of the active therapeutic substances at a site of action in an animal over said period, wherein each individual dose is independently tailored to optimize levels of the respective active therapeutic substances at the site of action for maximum efficacy as predetermined at commencement of said period, and wherein the time at which each dose is to be administered is tailored to a convenient schedule for said animal.

62. The drug delivery regimen of claim 61, wherein the ratio of active therapeutic substances to each other for each individual dose will be independently tailored to optimize levels of the active therapeutic substance at the site of action for maximum efficacy.

63. The drug delivery regimen of claim 61, wherein the ratio of the therapeutic substances to each other for each dose will not equal the ratio of the therapeutic substance to each other for at least one of the other doses, and wherein the ratio of therapeutic substances to each other for each individual dose is independently tailored to optimize levels of the active therapeutic substance at the site of action for maximum efficacy.

64. A drug delivery regimen, which comprises: an active therapeutic substance with a water-soluble phase and a non water-soluble phase administered during at least one 24 hour period of time to provide effective therapeutic levels of the active therapeutic substances at a site of action in an animal over said period, wherein the ratio of water-soluble phase to non water-soluble phase for each dose is independently tailored to optimize levels of the active therapeutic substance at the site of action for maximum efficacy as predetermined at commencement of said period, and wherein the time at which each dose is to be administered is tailored to a convenient schedule for said animal.

65. The drug delivery regimen of claim 64, wherein for each individual dose the ratio of the water-soluble phase to the non water-soluble phase will not equal the ratio of the water-soluble phase to the non water-soluble phase for at least one of the other doses, and wherein the ratio of water-soluble phase to non water-soluble phase for each individual dose is independently tailored to optimize levels for maximum efficacy.

* * * * *